US008877773B2

(12) United States Patent
Shekhar et al.

(10) Patent No.: US 8,877,773 B2
(45) Date of Patent: Nov. 4, 2014

(54) METHODS FOR TREATING CHRONIC OBSTRUCTIVE PULMONARY DISEASE

(75) Inventors: Anantha Shekhar, Indianapolis, IN (US); Philip L. Johnson, Indianapolis, IN (US)

(73) Assignee: Indiana University Research and Technology Corporation

( * ) Notice: Subject to any disclaimer, the term of this patent is extended or adjusted under 35 U.S.C. 154(b) by 0 days.

(21) Appl. No.: 13/503,609

(22) PCT Filed: Oct. 21, 2010

(86) PCT No.: PCT/US2010/053608
§ 371 (c)(1),
(2), (4) Date: Jul. 2, 2012

(87) PCT Pub. No.: WO2011/050199
PCT Pub. Date: Apr. 28, 2011

(65) Prior Publication Data
US 2012/0269810 A1    Oct. 25, 2012

Related U.S. Application Data

(60) Provisional application No. 61/254,689, filed on Oct. 24, 2009, provisional application No. 61/388,965, filed on Oct. 1, 2010.

(51) Int. Cl.
*A61K 31/44* (2006.01)
*A61K 31/42* (2006.01)
*A61K 31/17* (2006.01)
*A61K 31/438* (2006.01)

(52) U.S. Cl.
CPC ........ *A61K 31/438* (2013.01); *G01N 2800/301* (2013.01); *G01N 2800/52* (2013.01); *G01N 2800/56* (2013.01)
USPC ............ 514/300; 514/375; 514/299; 514/588

(58) Field of Classification Search
None
See application file for complete search history.

(56) References Cited

U.S. PATENT DOCUMENTS

| 2005/0048538 | A1 | 3/2005 | Mignot et al. | |
| 2008/0132490 | A1* | 6/2008 | Bergman et al. | 514/218 |
| 2008/0262046 | A1 | 10/2008 | Coleman et al. | |

OTHER PUBLICATIONS

Pastaka et al. European Journal of Internal Medicine 2007 (18) 524-530.*
Deng et al. Journal Applied Physiology 2007 (103) 1772-1779.*
Malherbe et al. Molecular Pharmacology 2009 (76) 618-631.*
Cox et al. Journal of Medicinal Chemistry 2010 (53) 5320-5332.*
Battaglia et al. Neuroscience and Biobehavioral Reviews 2005 (29) 169-179.*
PCT International Search Report and Written Opinion issued by the ISA/US in connection with PCT/US2010/053608 and completed on Jan. 17, 2011.
Deng at al., Contribution of orexin in hypercapnic chemoreflex: evidence from genetic and pharmacological disruption and supplementation studies in mice. J Appl Physiol. Nov. 2007, vol. 103, No. 5, p. 1772-9. Abstract; and p. 1774, Fig. 1.
Akbari at al., The selective orexin 1 receptor antagonist SB-334867-A impairs acquisition and consolidation but not retrieval of spatial memory in Morris water maze. Peptides. Mar. 2007, vol. 28, No. 3, p. 650-6. Abstract [online]. [Retrieved on Jan. 17, 2011]. Retrieved from the Internet: <URL: http://www.ncbi.nlm.nih.gov/pubmed> affinity 40 nM.
Chang at al. Inhibitory effects of an orexin-2 receptor antagonist on orexin A- and stress-induced ACTH responses in conscious rats. Neurosci Res. Mar. 2007, vol. 57, No. 3, p. 462 6. Abstract [online]. Retrieved on Jan. 17, 2011). Retrieved from the Internet: <URL: http://www.ncbi.nlm.nih.gov/pubmed>.
Malherbe at al., Biochemical and Electrophysiological Characterization of Almorexant, a Dual Orexin 1 Receptor (OX1)/orexin 2 Receptor (OX2) Antagonist: Comparison with Selective OX1 and OX2 Antagonists. Mol Pharmacol. Sep. 2009 (Epub Jun. 19, 2009), vol. 76, No. 3, p. 618-31.
Sakurai, "The neural circuit of orexin (hypocretin): maintaining sleep and wakefulness," Nat. Rev. Neurosci. 8:171-181 (2007).
Kayaba et. al., "Attenuated defense response and low basal blood pressure in orexin knockout mice," Am. J. Physiol. Regul. Integr. Comp. Physiol. 285:R581-R593 (2003).
Brisbare-Roch et al., "Promotion of sleep by targeting the orexin system in rats, dogs and humans," Nat. Med. 13:150-155 (2007).
Ferguson & Samson, The orexin/hypocretin system: a critical regulator of neuroendocrine and autonomic function, Front Neuroendocrinol. 24:141-150 (2003).
Johnson et al., "Neural pathways underlying lactate-induced panic," Neuropsychopharmacology 33:2093-210 (2008).
De Lecea et. al., "The hypocretins: hypothalamus-specific peptides with neuroexcitatory activity," Proc. Nat. Acad. Sci. USA 95:322-327 (1998).
Shekhar et al., "Orexin antagonists as potential therapeutic agents for panic disorder," Neuropsychopharmacology, vol. 31, No. 59, Dec. 4, 2006, p. S593.
Dias et al., "Antagonism of orexin receptor-1 in the retrotrapezoid nucleus inhibits the ventilatory response to hypercapnia predominantly in wakefulness," Journal of Physiology, vol. 587, No. 9, May 1, 2009, pp. 2059-2067.

* cited by examiner

*Primary Examiner* — Jeffrey S. Lundgren
*Assistant Examiner* — Michael Schmitt
(74) *Attorney, Agent, or Firm* — Armstrong Teasdale LLP

(57) ABSTRACT

Methods and compositions that down regulate the activity of orexins to treat panic disorder and panic-like responses associated with hypercapnic conditions are disclosed.

5 Claims, 38 Drawing Sheets

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
tctctacgaa ctgttgcacg ga                                    22

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
ctaaagcggt ggcggttgca gt                                    22

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
tccatttcaa cgaggaggac ttga                                  24

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
tgacgccgca gaaaaccacc ata                                   23

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
ctgtgaaggt gtaccccaat gtc                                   23
```

```
<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
atggcgttct tgaagagcgt cac                                              23

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
tatgttgccc tagacttcga gcaa                                             24

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
acggatgtca acgtcacact tcat                                             24
```

METHODS FOR TREATING CHRONIC OBSTRUCTIVE PULMONARY DISEASE

CROSS REFERENCE TO RELATED APPLICATIONS

This application is a U.S. national counterpart application of international application serial No. PCT/US2010/053608 filed Oct. 21, 2010, which claims priority to U.S. Provisional Patent Application No. 61/254,689 filed Oct. 24, 2009 and U.S. Provisional Patent Application No. 61/388,965 filed Oct. 1, 2010. The entire disclosures of PCT/US2010/053608, U.S. Ser. No. 61/254,689, and U.S. Ser. No. 61/388,965 are hereby incorporated by reference.

STATEMENT REGARDING FEDERALLY SPONSORED RESEARCH OR DEVELOPMENT

This invention was made with government support under MH052619, MH065702, and RR025761 awarded by the National Institutes of Health. The Government has certain rights in the invention.

INCORPORATION OF SEQUENCE LISTING

A paper copy of the Sequence Listing and a computer readable form of the sequence containing the file named 31377-22 (IURTC10041)_ST25.txt, which is 1,911 bytes in size (as measured in Microsoft WINDOWS® Explorer), are provided herein and are herein incorporated by reference. This Sequence Listing consists of SEQ ID NOS: 1-8.

TECHNICAL FIELD

The disclosure relates to the fields of neuroscience and psychiatry. In particular, the disclosure relates to methods and compositions for treating symptoms related to panic disorder and hypercapnic conditions.

BACKGROUND AND SUMMARY

A 'panic' response is a normal physiological survival reflex in humans and can be elicited by either an exteroceptive or interoceptive cue perceived as life-threatening. Panic disorder is characterized by recurrent episodes of severe anxiety accompanied by multiple physical symptoms such as increased cardiorespiratory responses. Panic disorder is also a risk factor for suicidal behavior.

The initial pathology in patients with panic disorder appears to be an alteration in central neural pathways regulating normal panic responses, thus rendering the patients susceptible to unprovoked panic symptoms when exposed to ordinarily mild stressors.

Panic attacks can be reliably induced in panic disorder patients in the laboratory by specific, normally innocuous interoceptive stimuli (e.g., intravenous 0.5M sodium lactate or yohimbine, or 7% $CO_2$ inhalations). These induced attacks are similar to spontaneously occurring episodes that characterized by sudden onset of fear symptoms along with rapid increases in respiration and heart rates. This indicates that global neural pathways that modulate arousal are perturbed in these patients. Consistent with this, reduced central GABAergic activity has been reported in subjects with panic disorder and drugs that restore GABAergic inhibition (e.g. benzodiazepines) have been used as treatments. Furthermore, acute disruption of GABAergic inhibition in panic-generating CNS sites such as the dorsomedial/periformical hypothalamus, amygdala or the dorsal periaqueductal grey leads to panic-like behavior and increased cardiorespiratory responses in rats. After chronically inhibiting GABA synthesis in the dorsomediaUperiformical hypothalamus of rats with 5 days of local 1-allylglycine (1-AG: a GABA synthesis inhibitor) infusions (using osmotic minipumps connected to a cannula directed at dorsomedial/periformical hypothalamus), sodium lactate challenges produce anxiety (measured by social interaction, elevated plus maze, open field test, and freezing in defensive probe burying test) as well as panic (characterized as increased "flight"-like locomotion and increased heart rate, mean arterial pressure responses). This is also pharmacologically validated with anti-panic drugs such as alprazolam, and provides a robust animal model of human sodium lactate-induced panic attacks.

Orexins (ORX), also called hypocretins (Hcrt), are neuroactive peptides that are produced by neurons located in the dorso-medial periformical and lateral hypothalamic areas of the brain. Orexin A and orexin B are hypothalamic peptides derived from a common precursor polypeptide called prepro-orexin. Human prepro-orexin mRNA encodes a 131-residue precursor peptide (prepro-orexin). The human prepro-orexin gene consists of two exons and one intron distributed over 1432 base pairs. The 143-base pair first exon includes the 5'-untranslated region and a small part of the coding region that encodes the first seven residues of the secretory signal sequence. The second exon contains the remaining portion of the open reading frame and 3'-untranslated region. Human pre-pro orexin mRNA has been characterized by Sakurai et al, J. Biol. Chem. 274(25): 17771-17776 (1999), the content of which is herein incorporated by reference in its entirety.

Prepro-orexin is processed to form pro-orexin, which is further processed to form orexin A and orexin B. Orexin A is a 33-amino acid peptide of 3562 Da with two sets of intrachain disulfide bonds. It has an N-terminal pyroglutamyl residue and C-terminal amidation. The primary structure of orexin A predicted from the cDNA sequences is completely conserved among several mammalian species (human, rat, mouse, cow, sheep, dog, and pig). On the other hand, rat orexin B is a 28-amino acid, C-terminally amidated linear peptide of 2937 Da that is 46% (13/28) identical in sequence to orexin A. The C-terminal half of orexin B is very similar to that of orexin A (73%; 11/15), whereas the N-terminal half is variable.

Orexin A and Orexin B are endogeneous peptides that activate orexin receptors, for example, orexin receptor type 1 (OX1R) and orexin receptor type 2 (OX2R), which are G-protein coupled receptors. Stimulation of these receptors by orexins causes an increase in intracellular calcium levels in hypothalamic cells in vitro. These hypothalamic neurons are the origin of an extensive and divergent projection system innervating numerous structures of the central nervous system.

ORX producing neurons in the dorsomedial/periformical and lateral hypothalamus and are known to regulate feeding, wakefulness and vigilance. It has been discovered herein that ORX neurons are involved in mobilizing sympathetic responses and desensitizing the parasympathetically mediated baroreflex to permit simultaneous increases of blood pressure and heart rates, which are all components of panic. These autonomic nervous system targets of ORX neurons are activated by sodium lactate infusions in sodium lactate panic prone rats but not in controls. Mice lacking the prepro-ORX gene have attenuated defense responses to panic cues and cardioexcitatory responses following disinhibition of the dorsomedial/periformical hypothalamus.

Acute hypercapnia (elevated arterial $CO_2$), rapidly increases extracellular pH when elevated levels of plasma $CO_2$ combine with water to form carbonic acid. Hence, the concentration of $CO_2$ in the blood is highly regulated and maintained within a very narrow range. Mild elevations of $CO_2$ initially increase respiration rate and tidal volume to help "blow off" excess $CO_2$. However, as $CO_2$ levels continue to increase, additional physiologic responses are initiated, including adaptive autonomic, behavioral and neuroendocrine responses. For instance, exposing rats to mildly elevated concentrations of hypercarbic gas (e.g., 7% $CO_2$) results in increased respiration rate and tidal volume that serve to reduce partial pressure of $CO_2$ ($PCO_2$) without mobilizing other components of the "panic-like" response. However, exposing rats to higher concentrations of hypercarbic gas (e.g., ≥10% $CO_2$) elicits additional components of a full blown panic-like response as evidenced by increases in sympathetic activity, hypertension, anxiety-like behaviors and mobilization of the hypothalamic-pituitary-adrenal (HPA) axis.

Acute hypercapnia (elevated arterial $CO_2$) can be life-threatening and rapidly mobilizes adaptive changes in breathing and behavioral arousal in order to restore acid-base homeostasis. Severe hypercapnia, seen acutely in sleep disorders (e.g., sleep apnea) or chronically in respiratory disorders (e.g., chronic obstructive pulmonary disease, COPD), also results in high anxiety and autonomic activation. Recent evidence has demonstrated that hypothalamic orexin (ORX: also known as hypocretin) neurons, which help to maintain waking states and vigilance, are Sensitive to local changes in $CO_2/H^+$ through acid-induced closure of leak-like K+ channels, and mice lacking prepro-orexin have blunted respiratory responses to hypercapnia.

Severe hypercapnia-induced autonomic hyperactivity and anxiety responses are relevant to managing hypercapnic conditions such as chronic obstructive respiratory disease (COPD), obstructive sleep apnea syndrome (OSAS), sudden infant death syndrome (SIDS), congestive heart failure, emphysema, asthma, bronchitis, pneumonia, cystic fibrosis, and alpha-1 antitrypsin, deficiency. In humans, even a single breath of air containing 35% $CO_2$ mobilizes sympathetic-adrenal responses and increases anxiety-like symptoms. However, the mechanism by which high $CO_2$ levels elicit panic-like responses is heretofore unknown.

Although the carotid body is the primary peripheral $CO_2$/ pH chemoreceptor, $CO_2$ readily crosses the blood-brain barrier to directly interact with central chemoreceptive neurons. Specialized $CO_2$/H+ chemosensory neurons with a high chemosensitivity (~300%, ~110% or ~120% increase in firing rate with 0.1 unit extracellular pH change, respectively) are found in medullary regions such as the retrotrapezoid nucleus, medullary raphe, and ventrolateral medulla. Without being bound by theory, it is believed herein that medullary chemosensitive neurons are important for regulating breathing following subtle changes in $CO_2$/H+ due to their proximity to major cerebral arteries and the brain surface. The ORX producing neurons, which are localized to the dorsomedial/perifornical (DMH/PeF) and adjacent lateral hypothalamus (LH) also display $CO_2$/H+-sensitive properties, but with lesser chemosensitivity (~100% increase in firing rate with 0.1 unit extracellular pH change).

Subjects with chronic episodes of hypercapnia (such as patients suffering from a chronic pulmonary disease including asthma, chronic obstructive pulmonary disease (COPD), pulmonary fibrosis, cystic fibrosis, and sarcoidosis) have significant co-morbidity with severe anxiety and sympathetic arousal, both of which can make management of these patients difficult. It is discovered herein that the orexin system plays an important role in responses to hypercapnia, particularly with concomitant severe anxiety. Current treatments of anxiety, such as fast acting benzodiazepine drugs, are not ideal for treating anxiety associated with hypercapnic conditions due to significant respiratory depression and other peripheral side effects. Thus, new therapies that can reduce or alleviate symptoms associated with panic disorder, anxiety, and hypercapnic conditions are desired.

DETAILED DESCRIPTION

Figure 1:
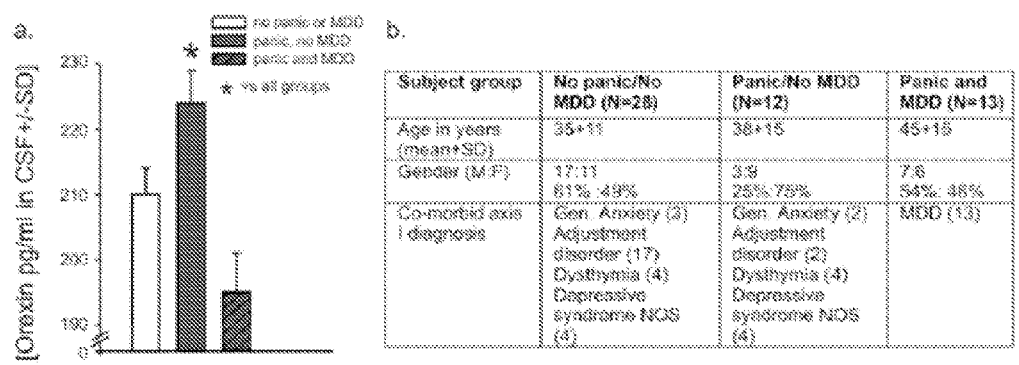
FIG. 1 shows orexin levels in cerebrospinal fluid of human patients.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein the term "pharmaceutically acceptable salt" refers to salts of compounds that retain the biological activity of the parent compound, and which are not biologically or otherwise undesirable.

As used herein, the term "treating" includes prophylaxis of the specific disorder or condition, or alleviation the symptoms associated with a specific disorder or condition and/or preventing or eliminating said symptoms.

As used herein the term "orexin activity" is intended to include binding of one or more orexins (e.g., orexin A or orexin B) to G-protein coupled orexin receptors (orexin 1 receptors and/or orexin 2 receptors) and activation of signal transduction pathways.

As used herein the term "chronic pulmonary disease" is intended to include any condition that occurs in the lungs or that causes the lungs to not work properly. Examples of chronic pulmonary disease include asthma, chronic obstructive pulmonary disease, pulmonary fibrosis, cystic fibrosis, and sarcoidosis.

As used herein the term "obstructive pulmonary disease" is intended to include any condition that restricts airflow to and from the lungs.

As used herein the term "chronic obstructive pulmonary disease" (COPD) refers to diseases of the lungs, including chronic bronchitis and emphysema, in which the airways become narrowed, limiting the flow of air to and from the lungs.

As used herein an "effective" amount or a "therapeutically effective amount" of an agent that downregulates orexin activity refers to a nontoxic but sufficient amount of an agent to provide the desired effect. For example, a desired effect would be preventing the onset, or reducing the severity, frequency or duration of symptoms associated with panic disorder and/or hypercapnia-induced anxiety or hypertensive response. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein the term "individual" without further designation is intended to encompass any warm blooded vertebrate domesticated animal (including for example, but not limited to livestock, horses, cats, dogs and other pets) and humans.

In one embodiment, a method of reducing one or more symptoms associated with panic disorder in an individual is described. The method comprises administering to the individual suffering from panic disorder a composition comprising a therapeutically effective amount of an agent to down regulate the activity an orexin at one or more orexin receptors.

In one embodiment, a method of treating symptoms associated with hypercapnia or a hypercapnic condition in an individual is described. The method comprises administering to the individual a composition comprising a therapeutically effective amount of an agent to down regulate the activity of an orexin at one or more orexin receptors.

In one embodiment, the method comprises administering an agent effective to reduce the expression of prepro-orexin. The expression of prepro-orexin may be reduced, for example, by a siRNA. Reducing the expression of preproorexin is understood to result in the reduction of orexin A and/or orexin B peptide levels and a decrease in activity at orexin 1 receptors and/or orexin 2 receptors.

In one embodiment, the method comprises administering a composition comprising an agent effective to reduce the expression of orexin 1 receptors. In one embodiment, the agent is effective to reduce the expression of orexin 2 receptors. The expression of orexin 1 receptors or orexin 2 receptors may be reduced for example, by a siRNA.

In one embodiment, the method comprises administering a composition comprising one or more orexin receptor antagonists. Illustrative examples of non-peptide orexin receptor antagonists include, but are not limited to, SB334867, SB408124, MK4305, almorexant, and those described in PCT Patent Application Publications WO 01/96302, WO 01/68609, WO 02/51232, and WO 02/51838.

In one embodiment, the method comprises administering a composition comprising an agent that antagonizes orexin 1 receptors. In one embodiment, the method comprises administering a composition comprising an agent that antagonizes orexin 2 receptors. In one embodiment, the agent antagonizes orexin 1 receptors and orexin 2 receptors. The agent may be a peptide or a non-peptide. Peptide agents include amino acid analogs, derivatives, and peptide mimetics.

In one embodiment, the agent is an antagonistic antibody or single chain antibody fragment that binds to orexin A. In one embodiment, the agent is an antagonistic antibody or single chain antibody fragment that binds to orexin B. It is appreciated that the antibody may bind to both orexin A and orexin B. In one embodiment, the agent is an antibody or antibody fragment that binds to orexin 1 receptors. In one embodiment, the agent is an antibody or antibody fragment that binds to orexin 2 receptors. It is appreciated that the antibody may bind to both orexin 1 and orexin 2 receptors.

Single-chain antibody fragments (scFv) that may provide a targeting mechanism to help drugs cross the blood-brain barrier are capable of being used either alone or in combination with an orexin receptor antagonist. For example, a human scFv that specifically binds to brain endothelial cell receptors and may pass through the blood-brain barrier is a suitable candidate. Drugs or drug carriers including orexin receptor antagonists can be attached to these scFv fragments and delivered into the brain.

Antibodies are also suitable for use as orexin receptor antagonists. For example antagonistic antibodies that target orexin receptors and able to cross the blood brain barrier are particularly well-suited. For example, antibodies capable of utilizing the receptor-mediated transcytosis systems are suitable. As examples, antibodies that recognize extracellular epitopes of receptor mediated endocytosis and also capable of specifically targeting or blocking orexin receptors are useful.

Additionally, such antibodies capable of crossing the blood-brain barrier may also be conjugated or linked to carry small molecule drugs as orexin receptor antagonists. Liposomes and liposomes containing siRNAs are also suitable for delivery of drugs to the brain either alone or in combination the antibodies discussed herein. Brain delivery of the RNA interference drugs via pegylated (polyethylene glycol attachment) immunoliposomes is also suitable.

In one embodiment, the hypercapnic condition is selected from chronic pulmonary disease, chronic obstructive pulmonary disease (COPD), obstructive sleep apnea syndrome (OSAS), sudden infant death syndrome (SIDS), sarcoidosis, Pickwick's syndrome, and/or congestive heart failure.

In one embodiment, hypercapnia symptom is selected from hypertension, anxiety, elevated sympathetic nervous system activity, and/or elevated respiration.

In one embodiment, the reduction in one or more symptoms of the panic disorder or hypercapnia is not accompanied by a general induction of sedation.

In one embodiment, a method of predicting whether an individual suspected of suffering from panic disorder will respond to a treatment to downregulate the activity of an orexin at one or more orexin receptors is described. The method comprises determining the levels of an orexin in a biological sample, and predicting that the individual will respond to the treatment if the orexin levels are higher in the individual compared to a control. In one embodiment, the biological sample is cerebrospinal fluid.

In one embodiment, a method of determining whether an individual is responsive to a treatment for panic disorder or a hypercapnic, associated disorder is described. The method comprises determining the levels of orexin in a biological sample from the individual during or after a treatment period, comparing the levels of orexin the sample to baseline levels prior to treatment, and determining that the individual is responsive to treatment if orexin levels are reduced during or after a treatment period. The treatment may include agents that directly or indirectly mediate orexin activity at one or more orexin receptors.

In one embodiment a method is provided for treating a hypercapnia-induced anxiety or hypertensive response. In one embodiment the method comprises administering a composition comprising an inhibitor of orexin activity. The composition can be administered prophylactically or can be administered at the onset of the symptoms. In one embodiment a method of treating symptoms associated with a patient suffering from a chronic pulmonary disease is provided wherein the method comprises administering to said patient a composition comprising an inhibitor of orexin activity. In one embodiment the chronic pulmonary disease is chronic obstructive pulmonary disease.

It is appreciated herein that compositions comprising one or more agents may include pharmaceutically acceptable carriers. Pharmaceutically acceptable carriers include any of the standard pharmaceutical carriers, such as a phosphate buffered saline solution, water, emulsions such as an oil/water or water/oil emulsion, and various types of wetting agents. Pharmaceutically acceptable carriers also encompass any of the agents approved by a regulatory agency of the US Federal government or listed in the US Pharmacopeia for use in animals, including humans.

It is appreciated herein that one or more agents may be in the form of a pharmaceutically acceptable salt.

It is to be understood that the composition may be administered orally or parenterally. Parenteral routes of administration include any means not through the alimentary canal, but by some other route including but not limited to, intranasal, inhalation, subcutaneous, intramuscular, intraventricular, intraspinal, intrarectal, or intravenous.

Utilizing an established panic model it is discovered herein that ORX-positive cells (specifically those in the dorsomedial/periformical hypothalamus) are activated (i.e., increased c-Fos) following sodium lactate administration in panic-prone rats, and was correlated with increases in anxiety-related behavior. This panic-related c-Fos expression was not observed in adjacent cells positive for melanin concentrating hormone.

It is also discovered herein that sodium lactate-induced panic responses are dependent on translation of the gene that produces ORX, preproOrexin. Translation of this gene was silenced by injecting small interfering RNA (siRNA) targeting the preproORX mRNA (siORX) (OnTargetP/us SmartPool® Dharmacon, Inc., Lafayette, Colo.) into the dorsomedial/periformical hypothalamus of panic-prone rats 48 h prior to sodium lactate or saline challenges. Quantitative RT-PCR was used to assess mRNA levels in the combined dorsomedial and lateral hypothalamus. Injecting panic-prone rats with siORX attenuated all components of the sodium lactate-induced panic-like responses (anxiety-like behavior, locomotor, and cardioexcitatory effects, whereas control rats displayed the predicted panic-like responses. The siORX treated rats had a small but significant reduction of blood pressure following saline. These rats had elevated baseline blood pressure. Treatment with siORX significantly reduced local preproORX mRNA in control and panic-prone rats compared to treatment with control siRNA. The effect was selective, as neither pro-dynorphin mRNA (a gene selectively co-expressed in ORX neurons; nor local pro-opiomelanocortin mRNA was reduced by siORX injection. Interestingly, panic-like responses following sodium lactate infusions appear to rapidly suppress both preproORX and pro-dynorphin mRNA levels in panic-prone rats compared to siCON challenged and control rats, which may suggest panic-induced negative feedback.

It is also demonstrated that sodium lactate-induced panic is attenuated by systemic pre-treatment with orexin receptor antagonists. A selective ORX1 receptor antagonist (SB334867, 30 mg/kg, Tocris) attenuated the anxiety-like behavior (measured with social interaction and open field tests. The ORX1 receptor antagonist also blocked the increases in locomotion, blood pressure and heart rate responses induced by the sodium lactate challenge. These effects mimicked the anti-panic effects that were observed when pre-treating the rats with alprazolam (3 mg/kg, Sigma, a clinically administered anti-panic benzodiazepine that blocks spontaneous and sodium lactate-induced panic attacks in patients. Similarly, a second ORX1 receptor antagonist (SB408124, 30 mg/kg, Tocris) also attenuated the sodium lactate-induced increases in locomotor activity and tachycardia responses in another group of panic-prone rats. The SB334867 ORX1 antagonist did not alter anxiety or cardiovascular responses in control rats or baseline measures in panic-prone rats.

A potential concern is that blocking ORX function might induce general somnolence or narcoleptic behavior, which may be the reason for the cessation of sodium lactate-induced panic responses. This may not be the case for the following reasons: acute blockade of ORX receptors did not result in narcoleptic states; and reducing ORX activity for short periods with either ORX 1 receptor antagonists or gene silencing did not result in somnolence during testing or alter baseline locomotor activity. In fact, the ORX gene silencing or an ORX1 receptor antagonist increased social interaction and exploration in the open field, clearly arguing against induction of sedation. In addition to its attenuation of panic-like responses, the ORX1 receptor antagonist (SB334867, 30 mg/kg i.p.) also blocks sodium lactate-induced freezing (indicative of panic-like fear) observed in the defensive burying test in panic-prone rats. This is not likely due to sedative effects of the ORX1 antagonist, since the number of mid-line crossings was not reduced in the treated panic-prone rats.

The sodium lactate-induced anxiety, but not the cardiorespiratory components of the panic response, appears to be linked to the bed nucleus of the stria terminalis. Therefore, to confirm an end target effect of activating ORX neurons, the bed nucleus of stria terminalis which receives ORX projections from the dorsomedial/periformical hypothalamus was focused upon. An ORX1 receptor antagonist (SB334867) was injected ipsilaterally into the bed nucleus of the stria terminalis of 1-AG treated panic-prone rats, prior to the sodium lactate challenge, which reduced anxiety-like behavior compared to the vehicle-injected rats.

The animal model of panic disorder utilized herein was established over the last 10 years and has robust face, predictive and construct validity. The model's predictive validity is demonstrated by responses, similar to those observed in patients with panic disorder, to both panic-inducing agents (e.g. sodium lactate, yohimbine, and inhalations of $CO_2$) and anti-panic effects of therapeutic agents such as alprazolam and group II metabotropic glutamate agonists. Also, this animal model was recently used in a series of preclinical studies to identify a novel class of translocator protein agonist (that enhances the central inhibitory effects of GABA), which subsequently showed anti-panic properties in clinical trials, further strengthening the model's predictive validity. The construct validity of this model is supported by the fact that neural circuits of the dorsomedial/periformical hypothalamus regulate behavioral and autonomic components of the "fight or flight" response in rats, and are implicated in eliciting panic-like responses in humans and animals. Furthermore, panic disorder patients have reported deficits in central GABA activity and pharmacological restoration of central GABA activity prevents panic attacks, in accordance with the animal model used herein. Also, the panic- and anxiety-like responses noted in this model are not likely due to a general increase in arousal, as there are no changes in baseline acoustic startle responses. Similarly, there is no increase in baseline startle response in human subjects with panic disorder. Therefore, the animal models used herein provide reasonable correlation to therapeutic effects of the methodologies used herein to individuals suffering from panic disorder.

The translational experiments in animal models and patients indicate that aberrant functioning of the ORX system underlies panic-attacks. Downregulation of ORX activity provides a novel therapeutic approach for the treatment of panic disorder.

Orexins also mediate hypercapnia-induced autonomic hyperactivity and anxiety responses psychological and physiological responses to hypercapnic conditions. As described herein, orexins play a role in the functional responses to acute exposure to 20% $CO_2$/normoxic gas. Exposing conscious rats to hypercapnic air resulted in pressor and bradycardic responses, enhanced anxiety-like behavior, increased cellular c-Fos responses in orexin neurons, and decreased hypothalamic ORX mRNA. Pre-treating rats with a centrally active inhibitor of orexin activity, the ORX1 receptor antagonist (SB334867 30 mg/kg, i.p.), attenuated hypercapnic gas-induced pressor and anxiety responses, without altering the robust bradycardia response.

Orexin has been discovered to be hyperactive during acute exposure to 20% $CO_2$/normoxic gas which leads to pressor and anxiety responses. Thus, downregulation of orexin activity at orexin receptors is a treatment option for treating hypercapnia-induced autonomic hyperactivity and anxiety responses.

The role of orexin in the functional responses to acute exposure to 20% $CO_2$/normoxic gas is described herein. Exposing conscious rats to such hypercapnic, but not atmospheric air, resulted in pressor and bradycardic responses, enhanced anxiety-like behavior, increased cellular c-Fos responses in orexin neurons, and decreased hypothalamic ORX mRNA. Pre-treating rats with a centrally active orexin receptor antagonist (30 mg/kg SB334867 i.p.) attenuated hypercapnic gas-induced pressor and anxiety responses, without altering the robust bradycardia response. Orexin receptor antagonists are useful to treat increased sympathetic drive and anxiety as seen in hypercapnic states such as COPD.

EXAMPLES

Example

Experiment 1. Orexin Levels in Human Cerebrospinal Fluid

To further validate the role of ORX in panic disorder, cerebrospinal fluid (CSF) samples were collected from 53 medication-free patients who presented with suicidal behavior. A cohort of subjects who presented with acute suicidal thoughts/behaviors was systematically assessed with psychiatric symptoms utilizing the comprehensive psychiatric rating scale (CPRS), and item 3 (inner tension) on that scale that assesses panic and anxiety. A threshold cut off at 1.5 on this scale was used to define a patient as having significant panic symptoms. Lumbar punctures were performed to collect cerebrospinal fluid (CSF), and samples stored in −80° C. until assay performed. CSF-ORX-A levels were measured using commercially available $^{125}$I radioimmunoassay (RIA) kits (Phoenix Pharmaceuticals) using protocols provided by Phoenix Pharmaceuticals. Duplicate samples were assayed and levels were determined against a known standard. All patients with substance abuse and traces of medication in the blood were excluded from the analysis. Increased CSF ORX was observed in patients with panic anxiety compared to subjects without panic anxiety. Furthermore, patients with only panic anxiety had significantly higher CSF ORX than subjects with panic anxiety and co-morbid major depressive disorder (see FIG. 1 for details). Increased ORX levels are therefore present in patients with panic anxiety.

Analyses of the CSF ORX levels (FIG. 1a) using Kruskal-Wallis ANOVA showed significant differences between the groups, P=0.004. Patients with panic and without MDD had the highest CSF orexin levels compared to both patients with panic and co-morbid MDD (Mann-Whitney U-test, p=0.002, two-tailed) and patients without panic (p=0.01, two-tailed). Age and gender did not have any impact on CSF ORX levels (Pearsons R and Mann-Whitney U-tests, P>0.1).

Example

Experimental Materials and Methods for Preclinical Experiments

Animals and housing conditions: All experiments used adult male Sprague-Dawley rats (300-350 g, Harlan Laboratories). Rats were housed individually in plastic cages under standard environmental conditions (22° C.; 12/12 light/dark cycle; lights on at 7:00 A.M.) for 7-10 days prior to surgery. Food and water were provided ad libitum. Animal care procedures were conducted in accordance with the *NIH Guidelines for the Care and Use of Laboratory Animals* (NIH Publication no. 80-23) revised 1996 and the guidelines of the IUPUI Institutional Animal Care and Use Committee.

Radio-Telemetry for Measuring Cardiovascular and Locomotor Responses:

Telemetry probes (Data Science International, St. Paul Minn.) were surgically implanted into the abdomen of anaesthetize rats to measure locomotor responses. Cardiovascular responses were measured by a femoral arterial line connected to the telemetric probe which contained a pressure transducer (Data Science International, St. Paul Minn.).

Inducing Panic Prone State in Rats:

After 3 days of recovery from telemetric probe surgery, cannulae (Plastics One Inc., Ranoake Va.) were directed at cardioexcitatory regions of the dorsomedial/periformical hypothalamus (DMH/PeF) which was connected, via PE-60 tubing, to an osmotic minipump (DURECT Corporation) filled with 1-AG solution (a glutamic acid decarboxylase inhibitor) or when applicable d-allylglycine (d-AG: the inactive isomer of 1-AG). The minipump was then sutured into place subcutaneously at the nape of the neck. The concentration of the solutions was such that 3.5 nmol/0.51 per hour of 1-AG or d-AG was infused continuously into the DMH/PeF region for the remainder of the given experiment. In the case of the siRNA experiments specialized T-cannulae were implanted permitting access to a removable 28 g injector to direct siRNA injections to the same location as the 1-AG infusions. Additionally these rats had guide cannulae directed to the opposite DMH/PeF for bilateral infusion of siRNA.

Description of Hypertonic Sodium Lactate (NaLac) or Isotonic Saline Infusion:

Rats received intravenous (i.v.) infusions (10 ml over 15 min of either 0.5M NaLac or 0.9% isotonic saline (when applicable)) using a syringe pump at least five days following the initiation of 1-AG or d-AG infusions. Once a stable baseline was achieved, i.v. infusions began and cardiovascular and activity data were recorded for 15 min (similar to clinical NaLac infusions).

Surgical Procedures and Osmotic Minipump Infusions:

Prior to and during surgery, rats were anesthetized with a nose cone connected to an isoflurane system (MGX Research Machine; Vetamic, Rossville Ind.). Rats were fitted with femoral arterial catheters for measurement of mean arterial blood pressure (MAP) and heart rate (HR) and with venous catheters for i.v. infusions.

Cardiovascular responses (i.e., MAP and HR) were measured by a femoral arterial line connected to a telemetric probe which contained a pressure transducer (Cat. no. C50-PXT, Data Science International (DSI) St. Paul Minn.). DSI DATAQUEST software was used to monitor and record MAP and HR. MAP and HR were recorded continuously in freely moving conscious rats and are expressed as a 20 min time course. The data reported are changes in HR and MAP from the average of the baseline (t−5 to t−1) from each rat.

After 3 days of recovery, animals were tested for baseline cardiovascular responses to lactate. Following baseline testing, rats were anesthetized 26 gauge T-shaped cannulae (Cat. no. 3260PG, Plastics One Inc., Ranoake Va.) were directed at cardioexcitatory regions of the dorsomedial/periformical hypothalamus (DMH/PeF, see reference 2) based on the following coordinates (from bregma: 1.2 mm posterior, +2.1 mm lateral, +9.1 mm ventral and adjusted for approaching at a 10 degree angle toward the midline with the stereotaxic incisor bar elevated 5 mm above the interaural line). The 26 gauge vertical arm of the T-shaped cannula was used for BMI injections while a 22 gauge side arm was attached, via PE-60 tubing, to an osmotic minipump for 1-AG or d-AG infusions (DURECT Corporation, Model no. 2002). Once the cannula was placed at the coordinates targeting the DMH/PeF, 50 pmol/100 nl of the GABAA receptor antagonist BMI was injected through the 22 gauge vertical arm of the guide cannula using a 33 gauge injection needle (cat. no. C315I, Plastics One Inc.) to ascertain that the tip of the cannula was placed in a cardioexcitatory region (i.e., where BMI elicits ≥50 beats/min in HR). This microinjection protocol commenced only after a stable baseline HR and MAP had been established for ~10 min. Following the injection, the guide cannulae were retracted; filled with either the 1-AG or d-AG solution; and cemented into place after being redirected to the previous stereotaxic coordinates. The minipump was attached to the cannula assembly with PE-60 tubing filled with either the 1-AG or d-AG solution; sutured into place subcutaneously at the nape of the neck. The concentration of the solutions was such that 3.5 nmol/0.5 µl per hour of 1-AG or d-AG was infused continuously into the DMH region for the remainder of the given experiment.

Social Interaction Test:

The social interaction (SI) test is a fully validated test of experimental anxiety-like behavior in rats. The apparatus itself consists of a solid wooden box with an open roof approximately 0.9 m long×0.9 m wide with walls 0.3 m high. All behavioral tests are videotaped with a camera above the box. The "experimental" rat and an unfamiliar "partner" rat are both allowed to individually habituate to the box for a 5 min period 24 h prior to each SI test. During the SI test, the two rats are placed together in the center of the box, and the total duration (sec) of non-aggressive physical contact (grooming, sniffing, crawling over and under, etc.) initiated by the "experimental" rat is quantified over a 5 min duration. A baseline SI test was performed 72+ h after i.v. catheterization, but prior to osmotic minipump implantation. Another SI test was performed 5 days following minipump infusions and immediately following saline or sodium lactate infusions. Videotaped sessions were scored at a later time by a researcher blinded to any drug treatment.

Open-Field Behavior Test:

The open-field arena covered an area of 0.9 m×0.9 m, with 0.4 m high walls. The open-field arena was divided into a 6×6 grid of equally-sized squares using black tape (36 total squares) with 4 squares forming the centre; 12 squares forming the middle perimeter; and 20 squares forming the outer perimeter. The test started by placing a rat in the centre. The behavior of each rat in the open-field arena was recorded on video and scored afterwards by an observer blind to the experimental treatment of each rat. Time spent in each region of the open-field was recorded.

Unconditioned Acoustic Startle Reflex Test:

Rats were placed into the startle chamber (35.6 cm wide× 27.6 cm deep and 49.7 cm high; model no. SM100SP, Hamilton Kinder, Poway, Calif.) and initially they received a 5-min acclimation period. Following the acclimation period, rats were presented with 30 startle-eliciting sounds (10 each at 90, 95 and 105 db) with a 30 sec interval between noise bursts (onset and offset of startle eliciting sounds are programmed and executed using Startle Monitor Windows NT/2000/XP Platform based software). The vendor reports that this system has an accurate noise stimulus that uses a high precision circuit providing +/−1 dB accuracy at all points of the scale (57-120 dB) and from chamber to chamber. The presentation of the different startle-eliciting sounds were grouped into three noises per bin and within each bin the order is randomized, so that at the end of the first phase the animals have been exposed to 10 bins for a total of 30 noise bursts given in a random but equally balanced set. Response performance was measured with a Piezo transducer calibrated and reported in newtons +/−1% full scale (Rat insert and sensing plate, model no. SM2002, Hamilton Kinder).

Defensive Burying Test

The defensive burying test is a validated test of experimental anxiety and defensive-like behavior in rats. For four consecutive days before defensive burying test (days 3, 4, 5 and 6 post 1-AG onset), rats were acclimated to the testing apparatus by placing them for 10 min in the testing cage (a polycarbonate rat housing cage, 30.5 cm width×30.5 cm height× 61 cm length) with 2.5 cm of bedding covering the floor and a small hole centered on a short dimension of the cage 2.5 cm above the bedding to accommodate the deactivated shock probe. The shock probe was 1 cm in diameter and extended 6 cm into the cage. Along the entire length of the exposed probe, 2 un-insulated wires were wrapped in parallel (not touching) so that the rat could not touch the probe without getting a shock. On testing day 7 post 1-AG onset), the un-insulated wires of the prod were connected to a LaFayette precision shock source (LaFayette Instruments Co., Model 5806). The shock intensity was set at 0.7 mA for the entire duration of testing so that the rat received a shock whenever the prod was contacted with its forepaws or snout. Immediately following the offset of an i.v. infusion, rats were placed individually in the test cage away from the shock probe (near short dimension side of cage that did not have probe) and 10 min sessions were videotaped for later assessment of defensive burying behavior. Time spent burying, in proximity of probe, grooming (30.5 cm width×61 cm length cage was divided into two 30.5×30.5 areas; one near probe and one distal from probe) and freezing as well as number of center line crossings were assessed. Behavioral assessments were made using software (ODLog Macropod Software for Windows, version 2.5.2) with different keystrokes coupled to each defensive behavior to accurately measure incidence and duration of each. The repertoire of behavioral reactions during a defensive burying test is well delineated and catalogued in rats. These behaviors include: 1) burying behavior, defined as duration spent pushing, shoveling, flicking and digging sawdust towards and around the prod with rapid movements of the snout and forepaws; 2) Freezing, defined as immobility with the body motionless; 3) probe exploration, defined as time spent on half of cage with probe; 4) rearing, defined as raising the body on the hind limbs in a vertical position; 5) ambulations, defined as number of times rat crossed from side of cage with probe to other; and also 5) grooming, defined as face washing, scratching, tail biting and licking of the body.

Example Experiment 2 c-Fos Induction in ORX Neurons of 1-AG and d-AG Treated Rats Following Infusions of NaLac or Saline Immunohistochemistry Perfusion:

Methods for perfusion and for verification of cannulae placements in experiment 12 were performed following procedures discussed herein. Briefly, 1-AG or d-AG treated rats received i.v. infusions of either lactate or saline vehicle over 15 min (n=6/group for 4 groups), were immediately tested in the SI test, then anesthetized and perfused with a 4% paraformaldehyde/1.5% sucrose solution and processed for immunohistochemistry 90 min following the onset of the i.v. infusions.

Double Immunohistochemistry:

In the present study, two of the six alternate sets of 30 µm coronal hypothalamic sections were stained for c-Fos protein (rabbit anti-c-Fos-polyclonal, affinity-purified antibody, cat. no. PC38, Ab-5, Calbiochem; diluted 1:10,000) on day one and then either ORX (rabbit anti-orexin A-polyclonal, affinity-purified antibody, cat. no. PC345, Calbiochem; diluted 1:200) or melanin concentrating hormone (MCH: rabbit anti-MCH antiserum protein, cat. no. H-070-47, Phoenix Pharm. Inc.; diluted 1:2000) the following day. Brain sections from all rats were immunostained with the appropriate primary antibody in a single immunohistochemical run, rather than in batches, with large volume incubations to limit variability in the quality of immunohistochemical staining among brain sections.

Sections were washed in PBS and then incubated in 1% $H_2O_2$ in PBS for 20 min. Sections were washed in PBS then PBST then incubated 12-16 h in PBST with primary antibody. The following day, sections were incubated 2 h in the appropriate secondary antibody: biotinylated swine anti-rabbit IgG (c-Fos day 1, and orexin A or MCH day 2; cat no. E0353; DAKO, diluted 1:200). Sections were washed again for 30 min in PBST then incubated 1.5 h in an avidin-biotin-peroxidase complex (cat no. PK-6100, Vector Labs, diluted 1:200). Substrates for chromogen reactions were SG (c-Fos; cat. no. SK-4700, Vector Labs) or 0.01% 3,3'-diaminobenzidine tetrahydrochloride (ORXA or MCH, cat. no. D-5637, Sigma) in PBS containing 0.003% $H_2O_2$, pH 7.4. Substrate reactions were run for 20 min for all reactions. Brain sections were then mounted, dehydrated and coverslipped for later analyses.

Figure 2:
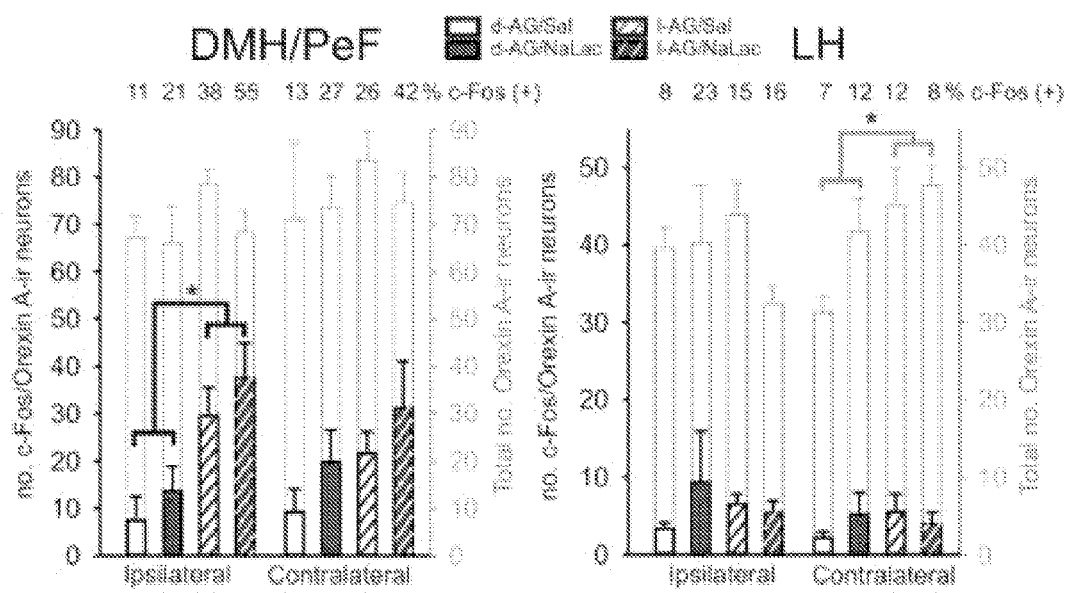
FIG. 2 shows c-Fos immunoreactive neurons in DMH/PeF and LH hypothalamic regions in panic-prone (1-AG treated) and control (d-AG treated) rats.
Figure 3:
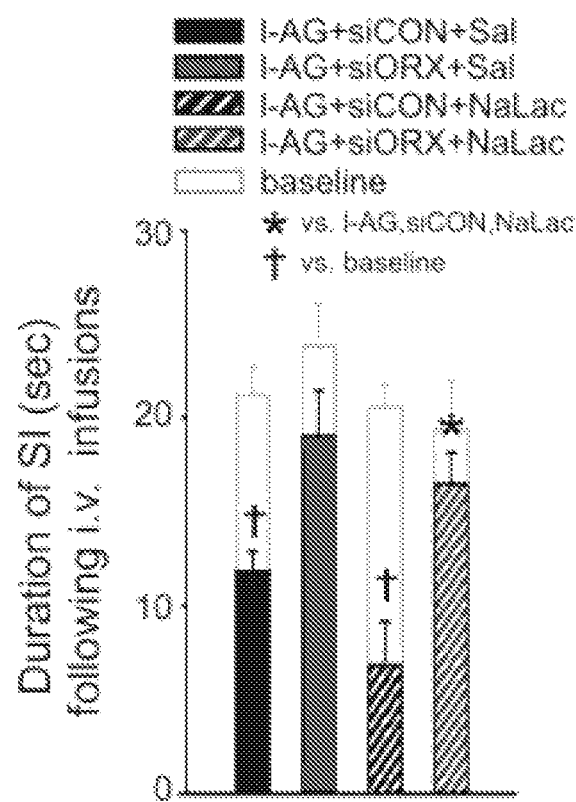
FIG. 3 shows social interaction in panic prone rats in response to injections of small interfering RNA targeting prepro-orexin (siORX) or control (siCON) and sodium lactate or vehicle.

Within the DMH, but not LH, only panic-prone rats had increased cellular responses in ORX (FIGS. 2-3; 1-AG effect, $F_{(1,20)}$=14.6, P=0.001), but not MCH neurons ipsilateral to the minipump, and these ORX, but not MCH responses, were correlated with changes in anxiety-related behavior. There was also an increase in the total number of ORX neurons in the LH contralateral to the 1-AG infusion when comparing d-AG/saline and 1-AG/saline treated rats (FIG. 2; 1-AG effect, $F_{(1,20)}$=7.4, p=0.013). Overall, these data are consistent with the hypothesis that removing GABAergic tone in the DMH alters local ORX neuronal activity to produce anxious rats that are prone to panic following lactate challenge.

Orexin A (ORX-A) producing neurons in the dorsomedial/periformical hypothalamus (DMH/PeF) display increased c-Fos immunoreactive (ir) neurons selectively in panic-prone (1-AG treated), but not control (d-AG treated), rats (n=6/group) (FIG. 2). 1-AG or d-AG treated rats received NaLac or saline challenge (n=6/group for 4 groups) as described above and were immediately tested in the social interaction (SI) test. 90 min following the SI test rats were perfused and brains were immunoprocessed into 6 parallel sets of coronal section (30 µm).

Example

Experiment 3. Injections of siORX or siCON into the DMH/LH Panic-Prone Rats Prior to Sodium Lactate or Saline Challenge or in Separate Control Rats In experiment 3, an RNAase free environment was maintained throughout the injection procedure and all injectors, syringes and tubing were exposed to RNaseZAP and rinsed thoroughly with RNA-free water prior to siRNA injections. A set of control rats were: anesthetized with Isoflurane® and received stereotaxic injections of OnTargetPlus SmartPool® siRNA against rat ppORX gene (siORX, 100 nMol, Dharmacon, cat. no. L-091285-00, Rat HCRT, NM_013179) into one side of the DMH/PeF, and negative control siRNA (siCON, 100 nMol, Dharmacon) into the other side of DMH/PeF (the side of each injection was counterbalanced) to confirm gene silencing; then sacrificed by rapid decapitation, following a brief (30 s) exposure to IsoFlurane® and 48 h after the siRNA injections. Rats with 1-AG minipumps and telemetric probes had siORX or siCON injected bilaterally through guide canulae opposite the 1-AG injector and through the minipump canulae ipsilateral to 1-AG infusion. 48 hrs after siORX or siCON treatment, these rats were exposed to saline or NaLac infusions (siCon/Sal n=4, siORX/Sal n=6, siCON/Lac n=5, siORX/Lac n=6) and SI behavioral and cardiovascular responses were recorded, and were then sacrificed by rapid decapitation, following a brief (30 s) exposure to IsoFlurane® 1 hr after the intravenous infusions.

RNA Isolation, Reverse Transcription and Quantitative Real-Time PCR.

Total RNA from DMH/PeF and LH dissected tissue was isolated using RNeasy micro kit (Qiagen). Extracted RNA was then reverse transcribed using the GeneAmp Gold RNA PCR kit (Applied Biosystems) at the following reaction conditions: 2.5 µM Oligo-dT primer, 2.5 mM magnesium, 250 mM of each deoxynucleotide triphosphate, 0.5 µ/ml of RNase inhibitor and final concentration of 0.75 U/µl of MuLV reverse transcriptase. The reverse transcription conditions were 10 min at room temperature, 15 min at 42° C., 10 min at 68° C. and 5 min at 95° C. and produced approximately 25 µl of product.

Beta-actin was used as a control for relative quantification. All samples were analyzed in triplicate for each gene. The PCR conditions were 1.5 mM $Mg^{+2}$, 0.5 mM of each primer, 0.2 mM of deoxynucleotide triphosphates using the SYBR Green kit (Applied Biosystems). PCR cycling conditions were 50° C. for 2 min, 95° C. for 10 min and 40 cycles of 95° C. for 30 s, 65° C. for 30 s, and 72° C. for 1 min on an ABI 7700 instrument. The uniformity of the PCR products was determined by dissociation curve analysis (Applied Biosystems) at the end of PCR.

RT-Q-PCR Quantification:

Standard curves of copy numbers based on size and absorbance at A260 were developed for each gene. Each unknown sample was extrapolated from these standard curves. Relative expression of the gene of interest in the samples is expressed as a ratio of copy number to beta-actin gene copy number.

TABLE 1

Gene, GI number, Forward primer 5' to 3', Reverse primer 5' to 3' and product size for prepro-orexin; pro-dynorphin; pro-opiomelanocortin (POMC) and beta-actin (b-actin).

| Gene | GI number | Forward primer 5' to 3' | SEQ ID NO | Reverse primer 5' to 3' | product size | SEQ ID NO |
|---|---|---|---|---|---|---|
| Prepro-orexin | NM_013179 | TCTCTACGAACTGTTGCACGGA | SEQ ID NO: 1 | CTAAAGCGGTGGCGGTTGCAGT | 227 | SEQ ID NO: 2 |
| Pro-dynorphin | NM_019374 | TCCATTTCAACGAGGAGGACTTGA | SEQ ID NO: 3 | TGACGCCGCAGAAAACCACCATA | 233 | SEQ ID NO: 4 |
| POMC | NM_139326 | CTGTGAAGGTGTACCCCAATGTC | SEQ ID NO: 5 | ATGGCGTTCTTGAAGAGCGTCAC | 250 | SEQ ID NO: 6 |
| b-actin | NM_031144 | TATGTTGCCCTAGACTTCGAGCAA | SEQ ID NO: 7 | ACGGATGTCAACGTCACACTTCAT | 219 | SEQ ID NO: 8 |

AG or 1-AG infusions correlated with changes in the duration of SI from baseline to post allylglycine infusions. In experiment 3, prior (48 h) injections of small interfering (si)

Figure 4:
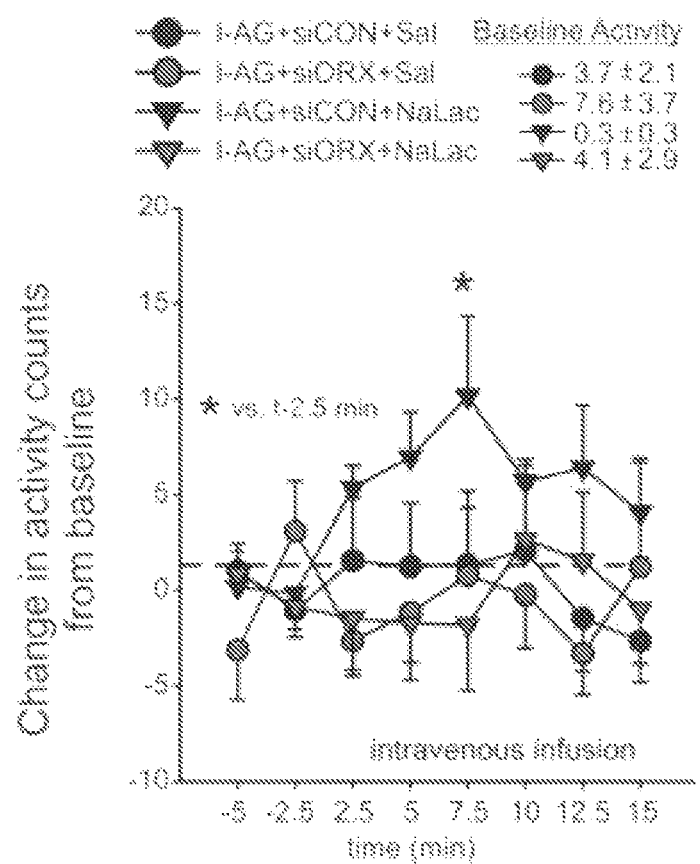
FIG. 4 shows locomotor activity in panic prone rats in response to injections of small interfering RNA targeting prepro-orexin (siORX) or control (siCON) and sodium lactate or vehicle.
Figure 5:
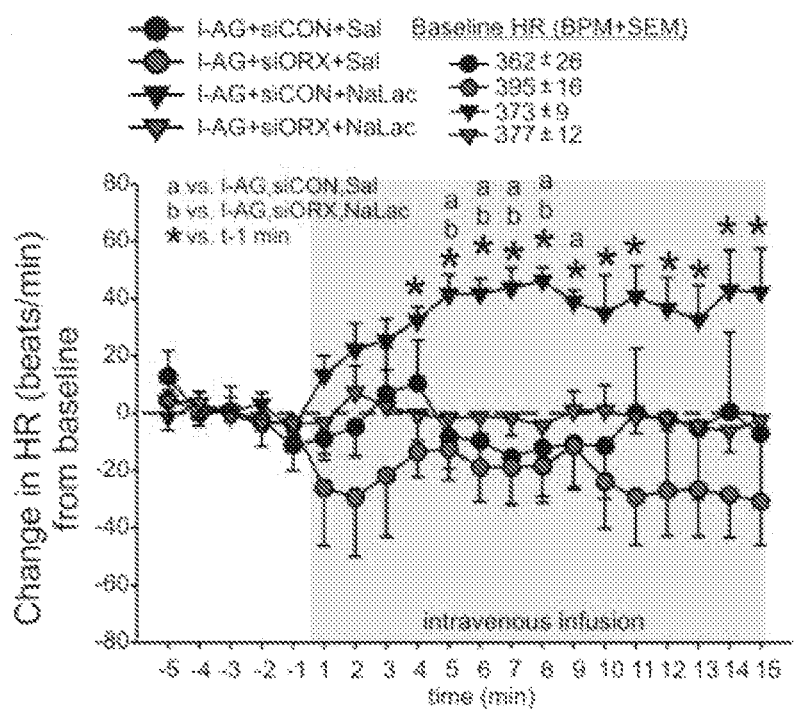
FIG. 5 shows heart rate in panic prone rats in response to injections of small interfering RNA targeting prepro-orexin (siORX) or control (siCON) and sodium lactate or vehicle.
Figure 6:
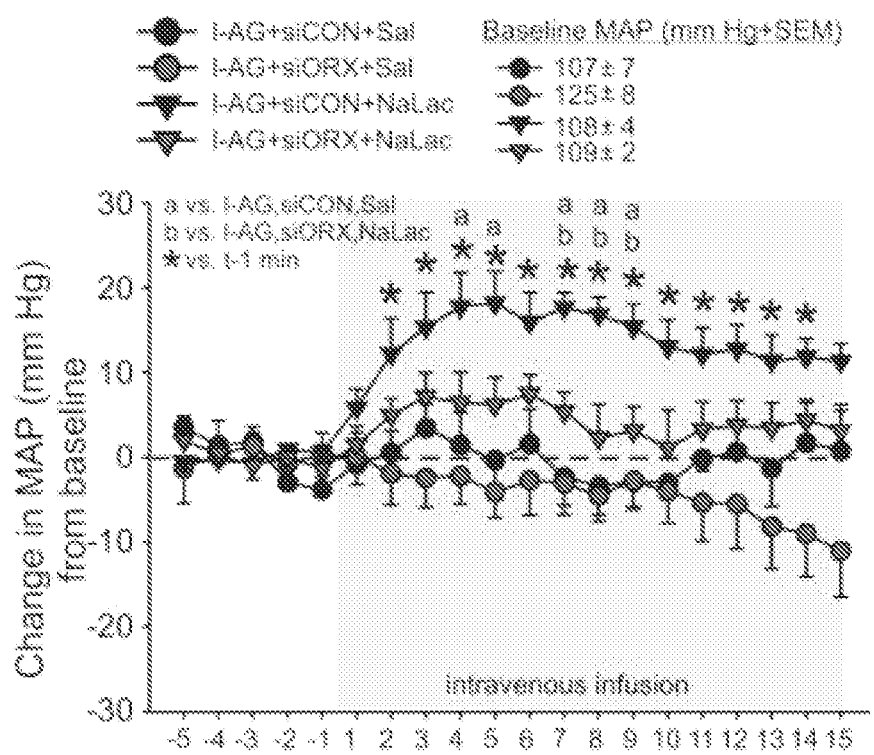
FIG. 6 shows mean arterial pressure in panic prone rats in response to injections of small interfering RNA targeting prepro-orexin (siORX) or control (siCON) and sodium lactate or vehicle

RNA targeting prepro-orexin mRNA (siORX), but not control siRNA (siCON), into the DMH/PeF of panic-prone rats (1-AG treated) attenuated 1-AG-induced (FIG. 3) anxiety-like responses (social interaction (SI) duration, n=5, 6, 5, 6; time×siRNA effect $F(1,18)=5.2$, $p=0.035$, * indicate Tukey's test and † indicates paired 2 tailed t-test, $p<0.05$) and 1-AG+lactate induced increases in (FIG. 4) general locomotor activity (increase over time $F(4,20)=4.1$, $p=0.014$ in only 1-AG+siCON+Vehicle group when assessing t−5 m to t+7.5 m), (FIG. 5) heart rate ((HR) increase over time in only the siCON+lactate group ($F(19,80)=4.6$, $p=0.001$) with time×siRNA ($F(19,323)=2.3$, $p=0.002$) and time×i.v. infusion ($F(19,323)=2.9$, $p=0.001$) interactions between groups) and (FIG. 6) mean arterial blood pressure ((MAP) increase over time $F(19,80)=6.3$, $p=0.001$ in only the siCON+lactate group with time×siRNA ($F(19,323)=2.2$, $p=0.003$) and time×i.v. infusion ($F(19,323)=5.5$, $p=0.001$) interactions between groups). For cardiovascular data, * (Dunnett's test) and a and b (Tukey's tests) indicate $p<0.05$.

Tissue Preparation and Micropunch for RT-PCR

All equipment and working surfaces were kept RNase free during dissection of the regions of interest. Frozen brains were sliced through the hypothalamus at 300 μm (coronal), using a Leica cryostat, and slices were placed onto microscope slides. Locations of injectors were verified in the slices using a Leica dissecting microscope set to 4× magnification. The DMH/PeF and lateral hypothalamus (LH) were dissected out of 2 adjacent 300 μm coronal brain slices using Microtome tissue micropunch (inside diameter=1.22 mm) at each location (bilateral DMH/PeF and LH). The DMH/PeF and LH tissue were immediately placed into 75 μl of RNAlater (Qiagen) and samples were placed on dry ice and kept at −80° C. overnight. Total RNA from DMH/PeF and LH dissected tissue was isolated using RNeasy micro kit (Qiagen). Extracted RNA was then reverse transcribed using the Gene-Amp Gold RNA PCR kit (Applied Biosystems) at the following reaction conditions: 2.5 μM Oligo-dT primer, 2.5 mM magnesium, 250 mM of each deoxynucleotide triphosphate, 0.5 μ/ml of RNase inhibitor and final concentration of 0.75 U/μl of MuLV reverse transcriptase. The reverse transcription conditions were 10 min at room temperature, 15 min at 42° C., 10 min at 68° C. and 5 min at 95° C. and produced approximately 25 μl of product.

The PCR conditions for both ppORX and beta-actin (endogenous control) were 1.5 mM Mg+2, 0.5 mM of each primer, 0.2 mM of deoxynucleotide triphosphates using the SYBR Green kit (Applied Biosystems). PCR cycling conditions were 50° C. for 2 min, 95° C. for 10 min and 40 cycles of 95° C. for 30 s, 65° C. for 30 s, and 72° C. for 1 min on an ABI 7700 instrument. The uniformity of the PCR products was determined by dissociation curve analysis (Applied Biosystems) at the end of PCR. All samples were analyzed in triplicate. Standard curves of copy numbers based on size and absorbance at A260 were developed for each gene. Each unknown sample was extrapolated from these standard curves. Relative expression of the gene of interest in the samples is expressed as a ratio of copy number to beta-actin gene copy number.

Figure 7:
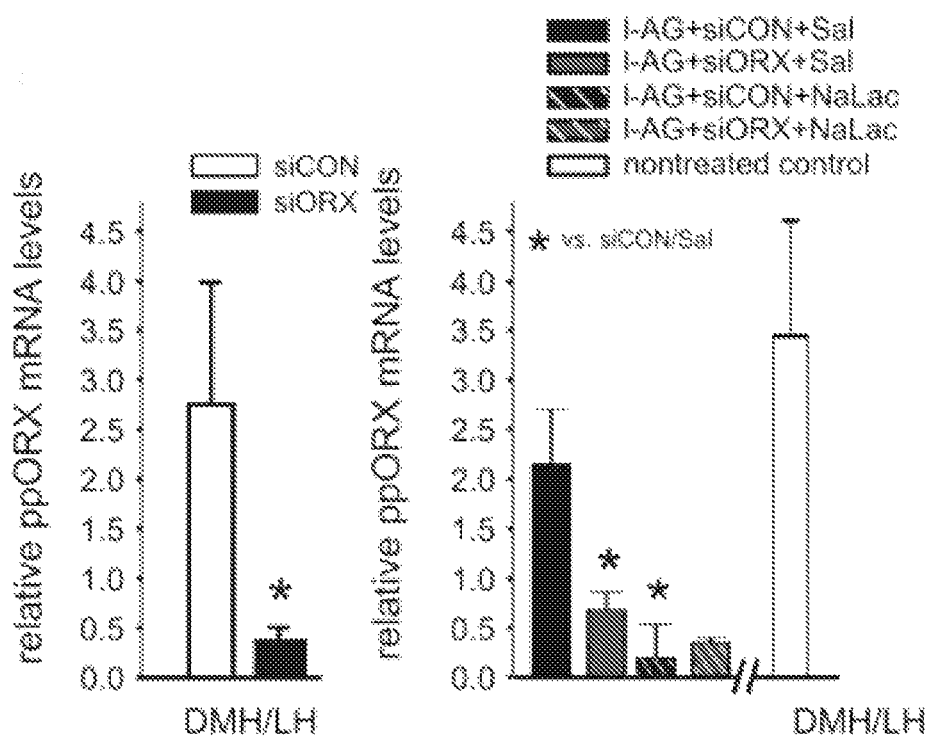
FIG. 7 shows prepro-orexin mRNA levels in DMH/LH in response to injections of siORX or siCON.
Figure 8:
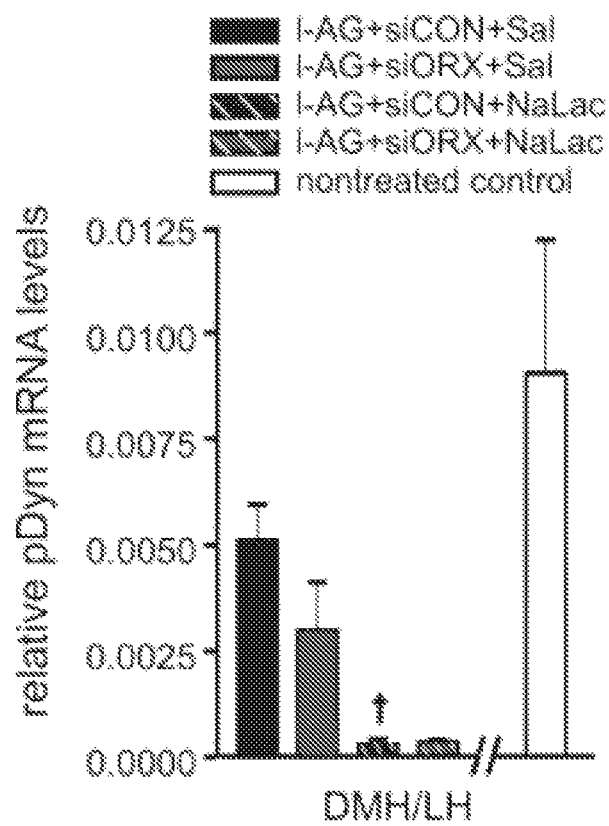
FIG. 8 shows pro-dynorphin (pDyn) mRNA levels in DMH/LH in response to injections of siORX or siCON.
Figure 9:
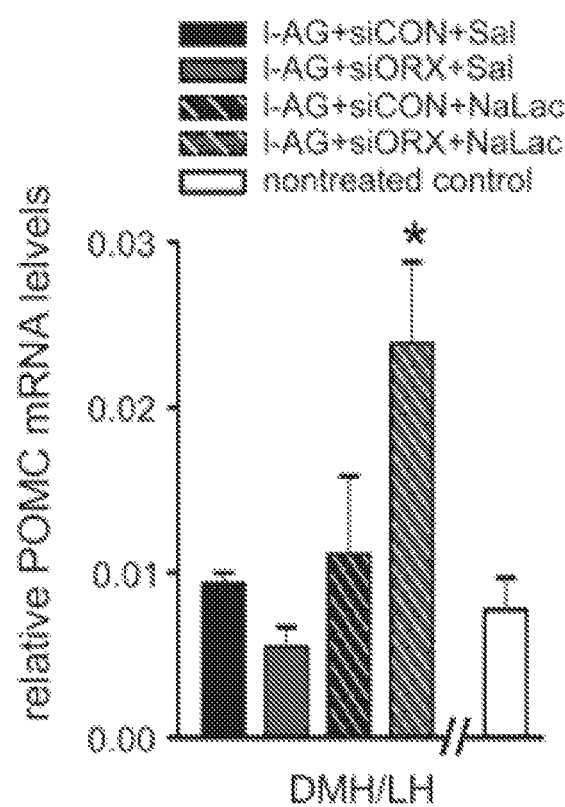
FIG. 9 shows pro-opiomelanocortin (POMC) mRNA levels in DMH/LH in response to injections of siORX or siCON.

Coronal illustration of unilateral 1-AG infusions (verified prior to micropunches) and bilateral siORX or siCON injections, and micropunches taken for later mRNA assays; 1) Injecting siORX into the DMH/PeF of control rats reduced concentrations of local prepro-ORX (ppORX) mRNA in the combined DMH/LH (* compared to siCON group injected on contralateral side, $t(8)=1.9$, $p=0.047$). Bilateral injections of siORX, but not siCON, into the DMH/PeF of panic-prone rats challenged with saline reduced local concentrations of (FIG. 7) ppORX (siRNA effect $F(1,18)=6.0$, $p=0.025$), but not (FIG. 8) pro-dynorphin (pDyn, siRNA effect $F(1,11)=1.8$, $p=0.184$,) or (FIG. 9) pro-opiomelanocortin (POMC, siRNA effect $F(1,11)=1.8$, $p=0.207$) mRNA in the DMH/LH. Challenging panic-prone rats (siCON or siORX treated) with lactate decreased m) local ppORX (i.v. infusion×siRNA interaction $F(1,18)=9.1$, $p=0.007$) and n) pDyn mRNA (i.v. infusion effect $F(1,11)=23.7$, $p=0.001$) and o) increased POMC (i.v. infusion effect $F(1,11)=9.2$, $p=0.012$) mRNA (* indicate $p<0.05$, compared to siCON+Sal group by Tukey's test). The last bar in FIGS. 7-9 represents the concentration of mRNA in the DMH/LH of untreated homecage control rats. All mRNA levels were determined by absolute quantitative RT-PCR and are expressed relative to absolute beta-actin mRNA levels. Abbreviations: contra, contralateral; DA, dorsal hypothalamic area; DMH, dorsomedial hypothalamus; ipsi, ipsilateral; LH, lateral hypothalamus.

Example

Figure 10:
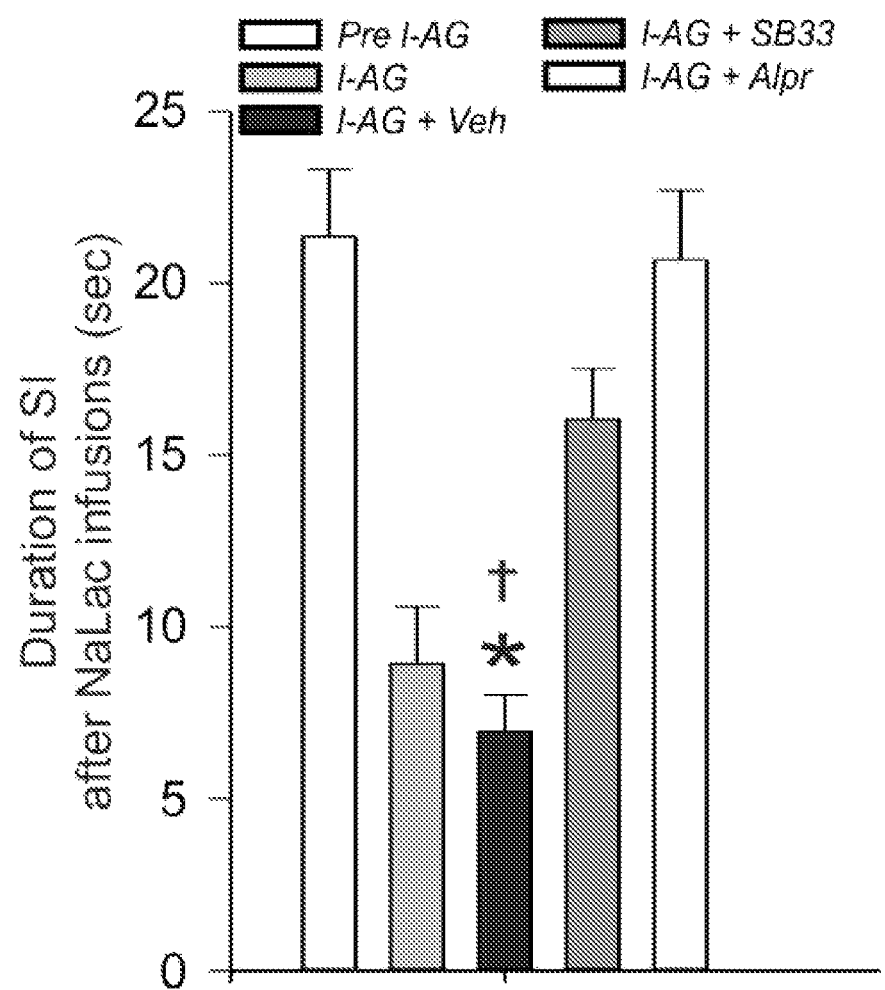
FIG. 10 shows social interaction after sodium lactate (NaLac) challenge in panic prone rats pre-treated with systemic injections of SB334867 (SB33) or alprazolam (Alpr).
Figure 11:
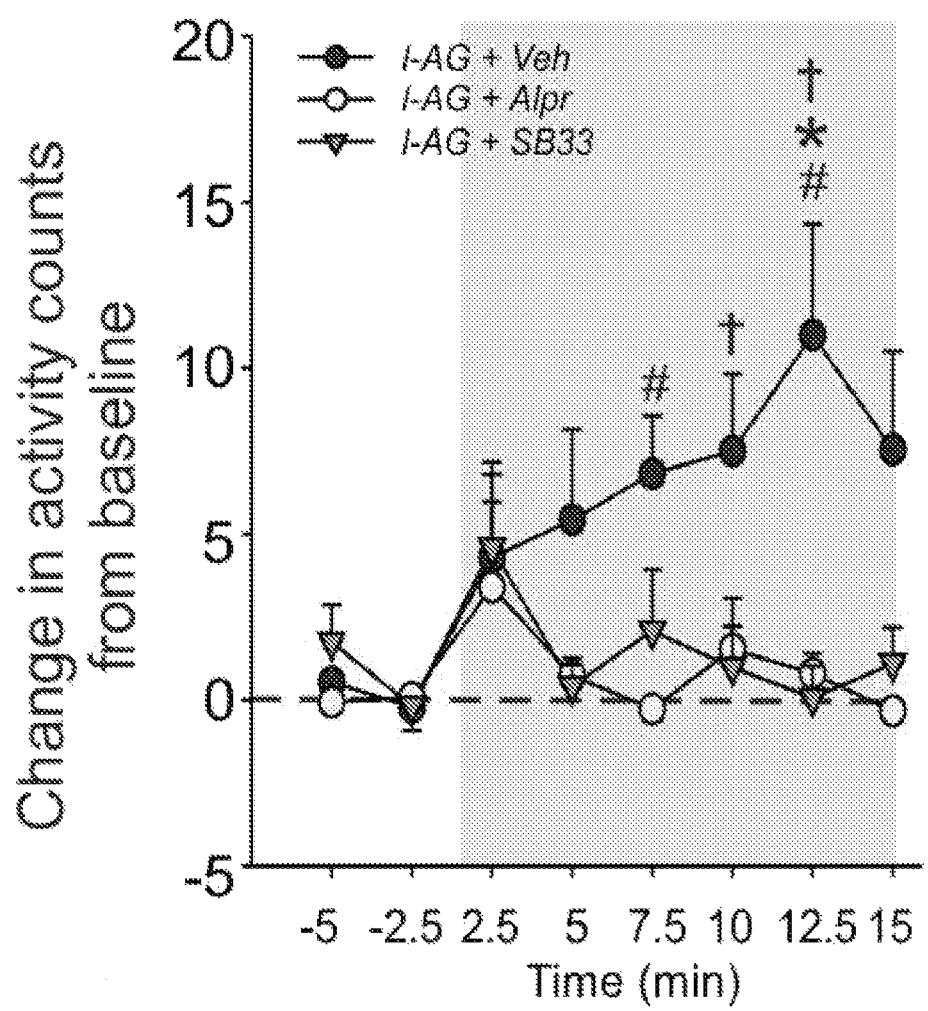
FIG. 11 shows locomotor activity after sodium lactate (NaLac) challenge in panic prone rats pre-treated with systemic injections of SB334867 (SB33) or alprazolam (Alpr).
Figure 12:
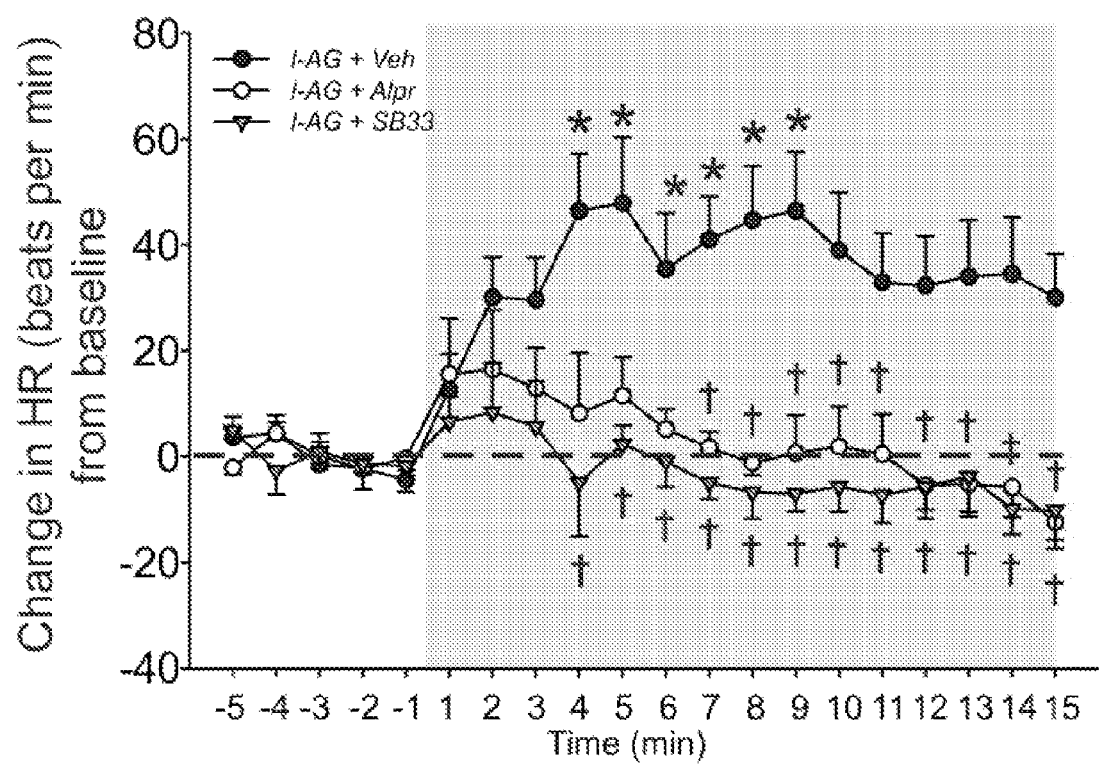
FIG. 12 shows heart rate after sodium lactate (NaLac) challenge in panic prone rats pre-treated with systemic injections of SB334867 (SB33) or alprazolam (Alpr).
Figure 13:
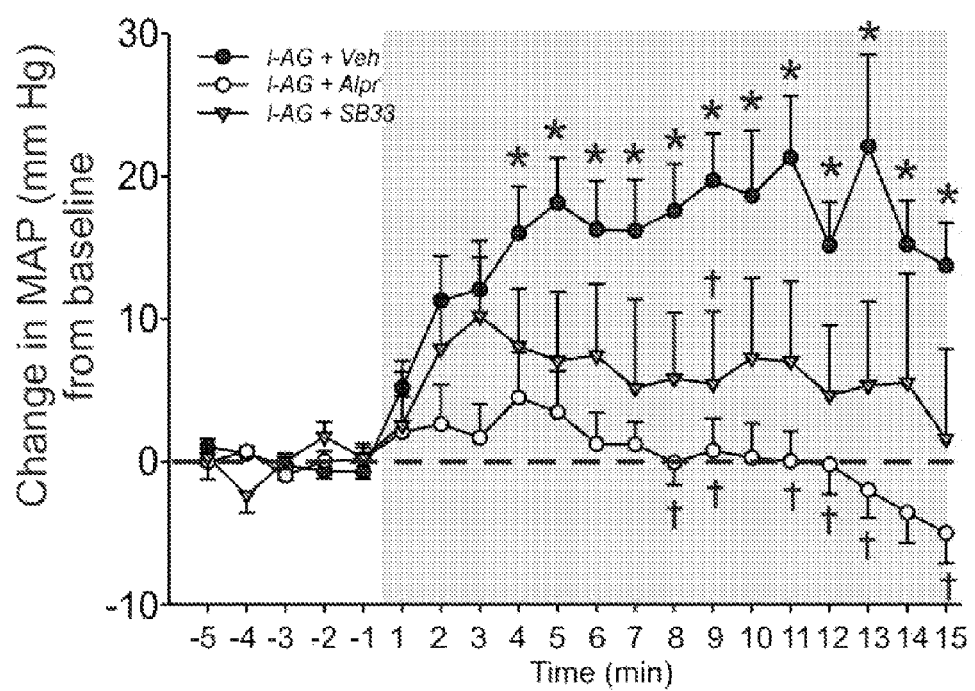
FIG. 13 shows mean arterial pressure after sodium lactate (NaLac) challenge in panic prone rats pre-treated with systemic injections of SB334867 (SB33) or alprazolam (Alpr).
Figure 18:
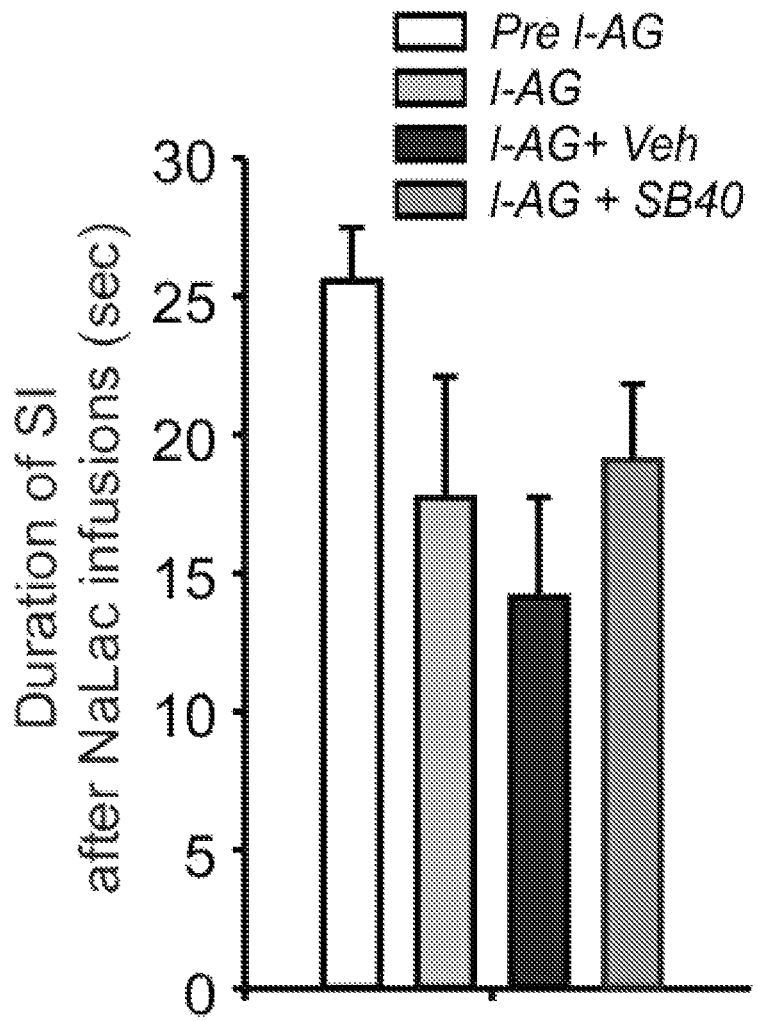
FIG. 18 shows social interaction after sodium lactate (NaLac) challenge in panic prone rats pre-treated with systemic injections of SB408124 (SB40).
Figure 19:
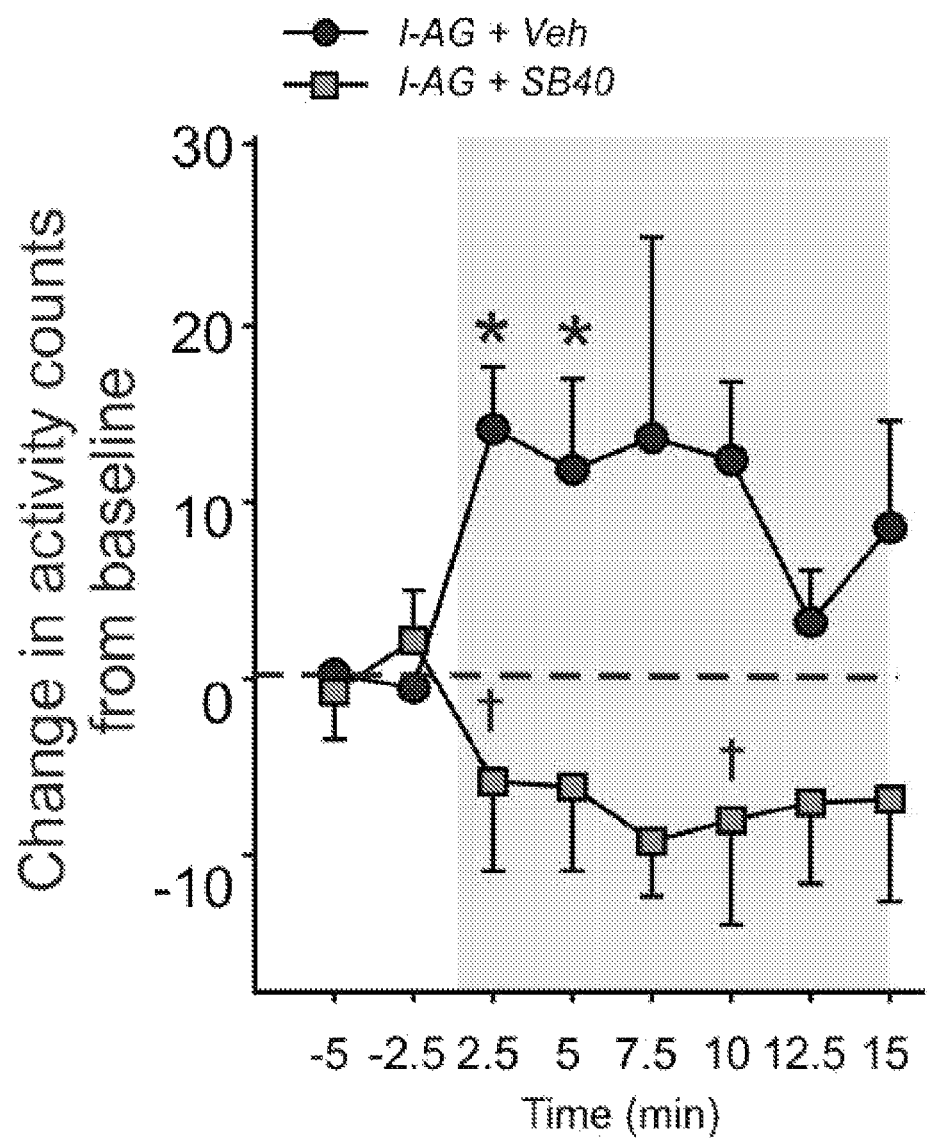
FIG. 19 shows locomotor activity after sodium lactate (NaLac) challenge in panic prone rats pre-treated with systemic injections of SB408124 (SB40).
Figure 20:
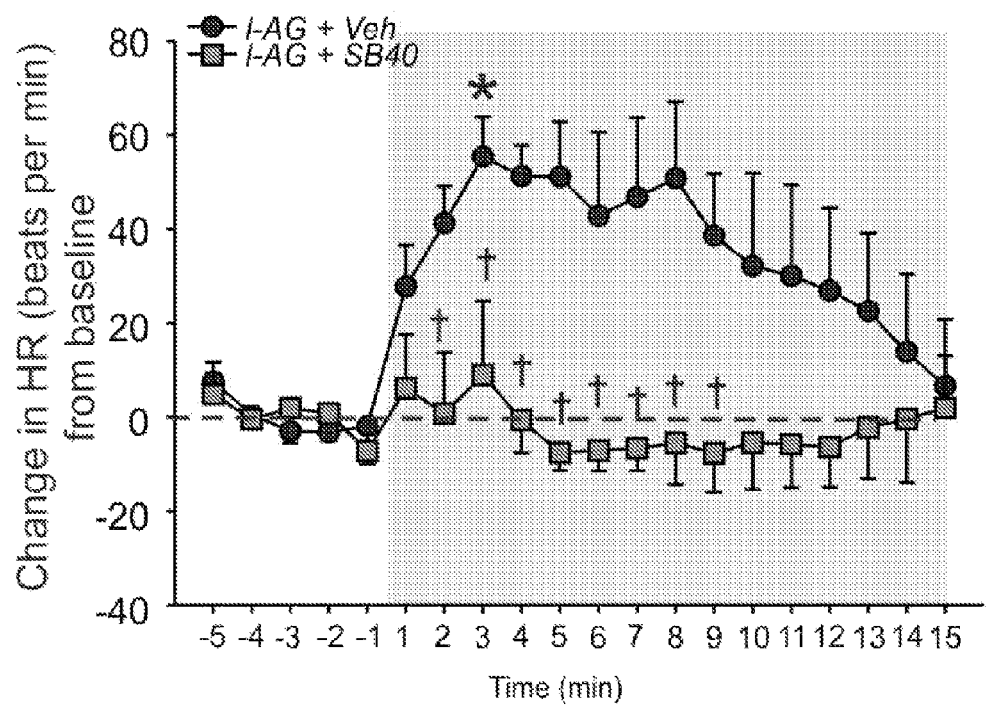
FIG. 20 shows heart rate after sodium lactate (NaLac) challenge in panic prone rats pre-treated with systemic injections of SB408124 (SB40).
Figure 21:
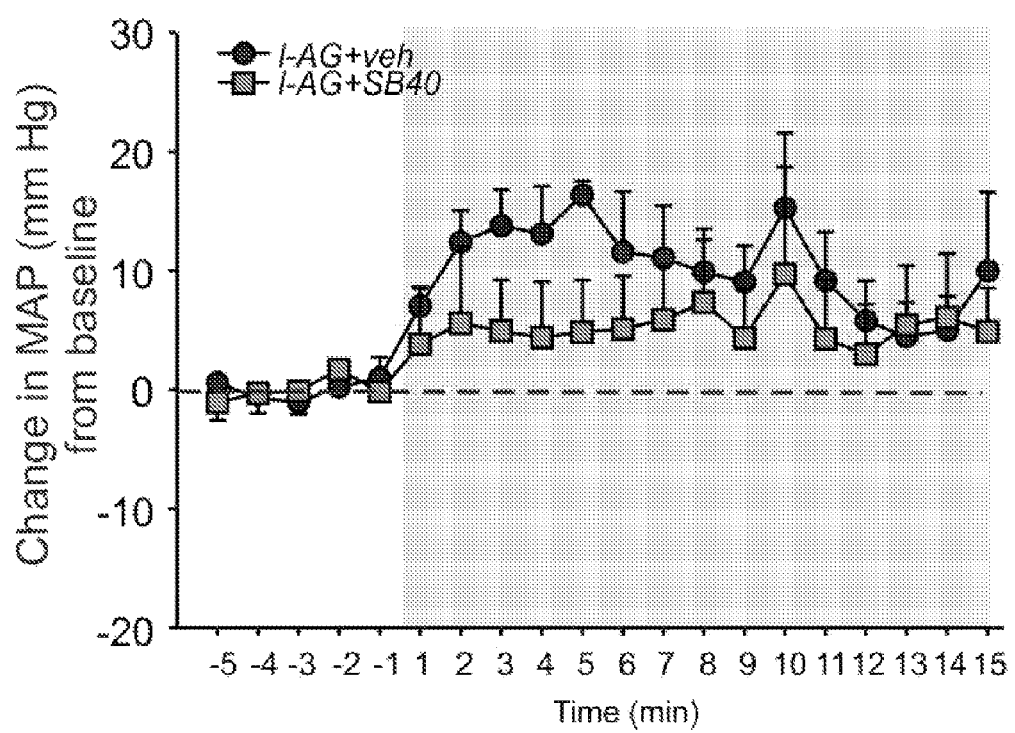
FIG. 21 shows mean arterial pressure after sodium lactate (NaLac) challenge in panic prone rats pre-treated with systemic injections of SB408124 (SB40).

Experiment 4. Pre-Treatment with Orexin Receptor Antagonist or Alprazolam on NaLac Induced Behaviors Systemically injecting the ORX1 receptor antagonist (SB334867) or benzodiazepine (alprazolam) into panic-prone rats prior to NaLac challenges attenuated (FIG. 10) anxiety-like responses (social interaction (SI) duration; n=12, 8, 11, 12, 6; treatment effect $F(4,44)=17.1$, $p=0.001$) and NaLac induced increases in (FIG. 11) general locomotor activity (n=10, 6, 10; treatment×time effect $F(14,161)=2.0$, $p=0.017$), (FIG. 12) heart rate (HR, n=12, 6, 11; drug×time effect $F(38,494)=3.9$, $p=0.001$), (FIG. 13) mean arterial blood pressure (MAP, n=12, 6, 10; drug×time effect $F(38,475)=2.7$, $p=0.001$). Similarly in experiment 5, systemically injecting SB334867 into panic-prone rats prior to NaLac challenges attenuated (FIG. 14) anxiety-like responses (decreased time spent in center of open field; n=8, 4, 6; one outlier detected in veh NaLac treated rats (Grubb's test, z value=1.89, $p<0.05$), treatment effect, Levene's test for homogeneity revealed unequal variance, $F(2,15)=9.6$, $p=0.002$ so a nonparametric a Kruskal-Wallis ANOVA/Mann-whitney U-test was $F(2)=7.4$, $p=0.025$) and NaLac induced increases in (FIG. 17) mean arterial blood pressure (MAP, n=5, 5; drug×time effect $F(19,152)=2.7$, $p=0.001$), and (FIG. 16) heart rate (HR, n=5, 5; drug×time effect $F(19,152)=0.6$, $p=0.873$). (FIG. 15) No change was detected in general locomotor activity (n=5, 5; drug×time effect $F(7,56)=0.9$, $p=0.480$). In experiment 6, systemically injecting a 2nd ORX1 receptor antagonist (SB408124) into panic-prone rats did not significantly alter (FIG. 18) the SI duration, or (FIG. 21) MAP, but did attenuate NaLac induced increases in (FIG. 19) locomotor activity (n=4, drug×time effect, $F(7,42)=3.6$, $p=0.004$) and m) HR (n=4/group, drug×time effect, $F(19,114)=3.7$, $p=0.001$). For anxiety tests in FIGS. 3, 10, and 18, * and + indicate significant differences between groups using a Tukey's HSD tests with $p<0.05$. For activity and cardiovascular data, * indicates significantly different from baseline using a Dunnett's test, † indicates significantly different using a paired t-tests for SB334867 in FIGS. 15-17 and SB408124 in FIGS. 19-21, and † and # indicate significant differences between groups using a Tukey's HSD tests for SB334867 in FIGS. 11-13 with $p<0.05$. Except for activity data in FIG. 15 ($t(4)=-2.9$, $p=0.043$), there was no significant baseline HR, MAP or activity between groups. Correct probe-placements were verified.

Figure 22:
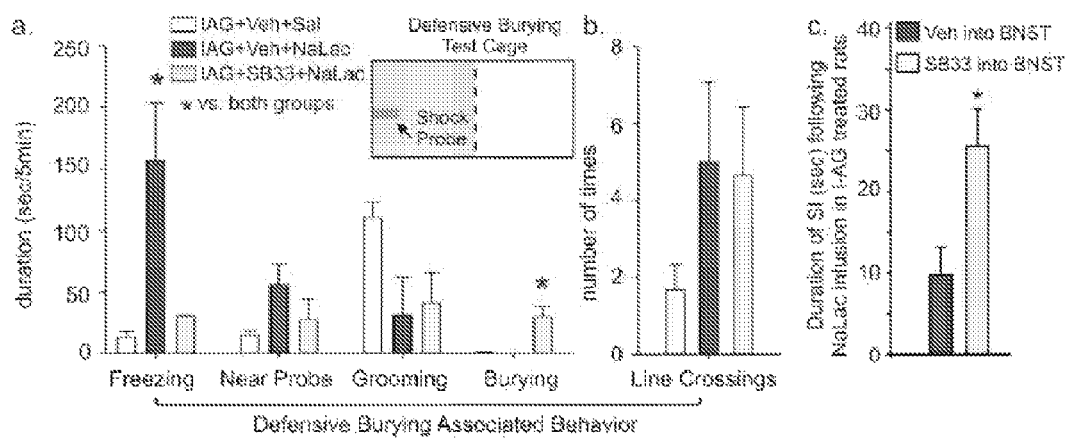
FIG. 22 shows defensive shock associated behaviors (a), line crossings (b), and social interaction (c) after sodium lactate challenge in panic prone rats pre-treated with SB334867 (SB33) or vehicle (Veh).

As shown in FIG. 22, experiment 8, assessment of defensive shock (DS) associated behaviors revealed that, compared to saline infused controls, 1-AG+NaLac+Vehicle (Veh) treated rats a) spent over half of the 5 min DS test immobile or "freezing" ($F(2,6)=7.9$, $p=0.021$), which was completely blocked in the 1-AG+NaLac group systemically treated with the SB334867 (SB33) ORX1 receptor antagonist (see FIG. 22a). Defensive shock test cage is illustrated in inset in FIG. 22a. An interesting finding was that, compared to the 1-AG+NaLac rats injected with SB334867, the 1-AG+sal and 1-AG+NaLac rats treated with vehicle spent little to no time burying during the test ($F(2,6)=12.1$, $p=0.008$). No differences were detected in time spent near probe ($F(2,6)=2.3$, $p=0.182$), rearing ($F(2,6)=1.2$, $p=0.360$), or grooming ($F(2,6)=3.1$, $p=0.112$) or (FIG. 22b) number of times crossed line dividing halves of test cage (i.e., probe side versus non-probe side ($F(2,6)=1.3$, $p=0.344$)). (FIG. 22c) Unilateral injections of the ORX1 receptor antagonist SB334867 (300 pmoles/100 nl) into the bed nucleus of the stria terminalis (BNST) of 1-AG treated rats prior to the lactate challenge restored the duration of SI to normal baseline levels, compared to SI duration following vehicle injection ($t(4)=6.9$, $p=0.0002$, n=5/crossover design: experiment 9). Bars in graphs represent the mean, and error bars represent the standard error of the mean. Infusion placements in DMH/PeF and injections sites into the BNST were verified.

Example

Experiments 5-7. Attenuating Panic-Like Responses with Systemic ORX1 Receptor Antagonists In experiments 4-6, rats were made panic vulnerable with 1-AG. 5 days after 1-AG onset, in a counterbalanced design, rats received intraperitoneal (i.p.) injections of treatment drug or vehicle 30 min prior to i.v. infusions. In experiment 4, rats were injected with the ORX1 receptor antagonist SB334867 (N-(2-Methyl-6-benzoxazolyl)-N'-1,5-naphthyridin-4-yl urea) (30 mg/kg, Tocris, in 0.2 ml/100 g volume DMSO, n=12), alprazolam (3 mg/kg, Sigma, in 0.2 ml/100 g volume DMSO, n=6) or vehicle (0.2 ml/100 g volume DMSO, n=11) 30 min prior to a NaLac challenge and, immediately after, a SI test was used to assess anxiety behavior. In experiment 5, baseline in an open field (OF) behavior test of anxiety was assessed (n=8) prior to 1-AG infusions. 5 days after 1-AG treatment, rats were split into 3 treatment groups, where groups received: i.p. vehicle+i.v. saline (n=5); i.p. vehicle+i.v. NaLac (n=5); or i.p. SB334867 (30 mg/kg)+i.v. NaLac (n=6). Immediately following the NaLac challenge, rats were placed in the OF test. 72 h later, this was repeated except that each rat received an alternative treatment, so that all rats received 2 of the 3 treatments (i.e., vehicle/saline and vehicle/NaLac; vehicle/NaLac and SB334867/NaLac; or vehicle/saline and SB334867/NaLac). In experiment 6, 1-AG treated rats received an injection of an alternative ORX1 receptor antagonist (30 mg/kg SB408124 (N-(6,8-Difluoro-2-methyl-4-quinolinyl)-N'-(4-(dimethylamino)phenyl)urea), Tocris, in 0.2 ml/100 g volume DMSO, n=4) or vehicle (0.2 ml/100 g volume DMSO, n=6) 30 min prior to NaLac. In experiment 7, control rats (no 1-AG or NaLac treatment) were assessed in a SI test. 48 h later these rats received an i.p. injection of an ORX1 receptor antagonist (30 mg/kg SB334867, Tocris, in 0.2 ml/100 g volume DMSO, n=7) or vehicle (0.2 ml/100 g volume DMSO, n=7) and 30 min post injection cardiovascular activity was monitored for 20 min followed by an immediate SI test.

Example

Systemic SB334867 or Alprazolam in Panic-Prone Rats Prior to Lactate Challenge Using Social Interaction to Assess Anxiety Behavior Adult male Sprague-Dawley rats were anesthetized and surgically implanted with telemetrical probes to measure cardiovascular activity prior to and during lactate infusions. After a 3 day recovery, rats were anaesthetized and had osmotic minipumps (previously filled with 1-AG) stereotaxically implanted unilaterally into the DMH. 5 days later, in a counterbalanced design, half of these rats received an intraperitoneal (i.p.) injection of the ORX1R antagonist, SB334867 [30 mg/kg, cat. no. 1960, Tocris, in 0.2 ml/100 g volume DMSO, n=12], alprazolam (3 mg/kg, Sigma, in 0.2 ml/100 g volume DMSO, n=6) or vehicle (0.2 ml/100 g volume DMSO, n=11) 30 min prior lactate challenge.

Prior i.p. injections of SB334867 and alprazolam, but not vehicle, attenuated all lactate induced panic-like responses in panic-prone (1-AG treated) rats [SI (n=14, 8, 11, 12, 6, drug effect $F_{(4,36)}=17.8$, $p=0.001$); Activity (n=10, 6, 10, drug×time $F_{(14,161)}=2.0$, $p=0.017$), HR (n=12, 6, 11, drug×time $F_{(38,494)}=3.9$, $p=0.001$); and MAP (n=12, 6, 10, drug×time $F_{(38,475)}=2.7$, $p=0.001$) (see FIG. 10-13]. Histology verified that all minipump cannulae were in the DMH/PeF region. Baseline analyses [Activity, $F_{(2,23)}=2.5$, $p=0.101$; MAP, $F_{(2,24)}=0.9$, $p=0.435$; HR, $F_{(2,26)}=6.3$, $p=0.006$, SB334867 and alprazolam baselines differed, but neither SB not alprazolam baselines differed between vehicle controls using Tukey's HSD posthoc].

Example

Systemic SB334867 in Panic-Prone Rats Prior to Lactate Challenge Using Open Field to Assess Anxiety Behavior All adult male Sprague-Dawley rats were anesthetized and surgically implanted with telemetrical probes to measure cardiovascular activity prior to and during lactate infusions. After a 3 day recovery, baseline open field behavior was assessed (n=8), then rats were anaesthetized and had osmotic minipumps (previously filled with 1-AG) stereotaxically implanted unilaterally into the DMH. 5 days later rats were split into 3 treatment groups (n=5/group), where each group received a prior intraperitoneal (i.p.) injection of the ORX1R antagonist, SB334867 [30 mg/kg, cat. no. 1960, Tocris, in 0.2 ml/100 g volume DMSO, n=6], or vehicle (0.2 ml/100 g volume DMSO, n=5) 30 min prior lactate. Immediately following the lactate challenge, the rats were assessed for anxiety using the open field test. Seventy two hours later, this was repeated except that each rats received an alternative treatment, so that all rats received 2 of the 3 treatments (i.e., Sal/Vehicle and NaLac/Veh; NaLac/Veh and NaLac/SB334867; or Sal/Veh and NaLac/SB334867).

Figure 14:
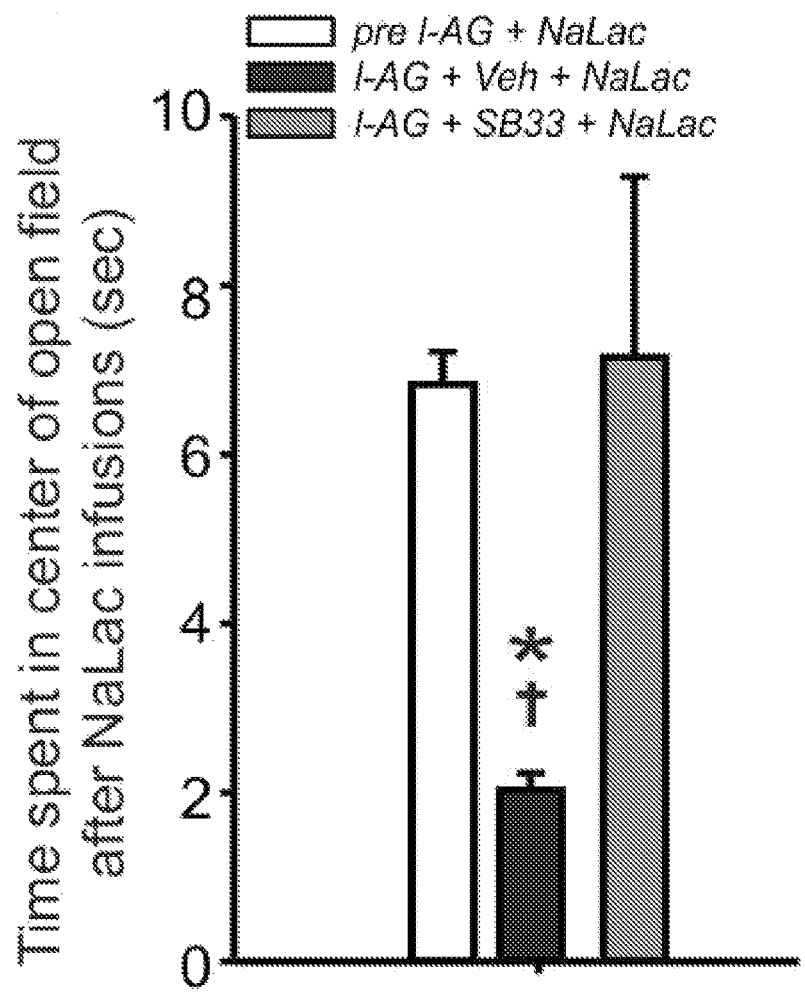
FIG. 14 shows open field test results after sodium lactate (NaLac) challenge in panic prone rats pre-treated with systemic injections of SB334867 (SB33).
Figure 15:
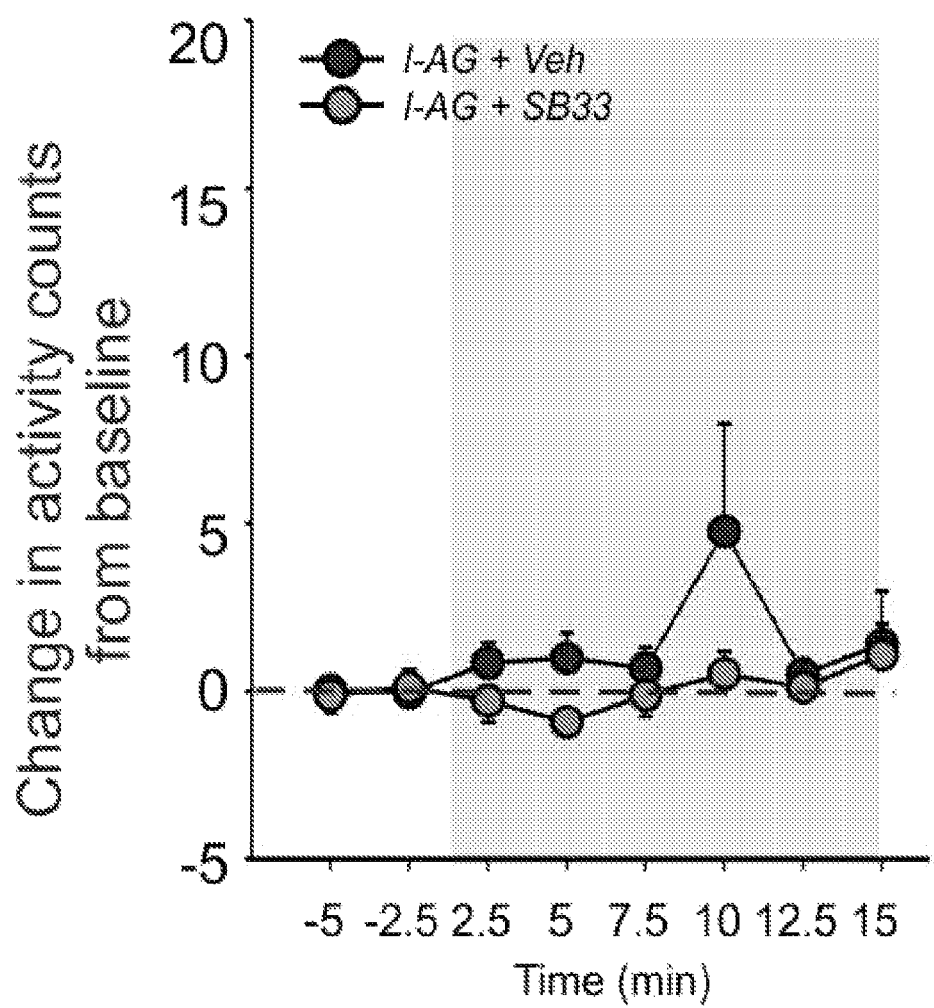
FIG. 15 shows locomotor activity after sodium lactate (NaLac) challenge in panic prone rats pre-treated with systemic injections of SB334867 (SB33).
Figure 16:
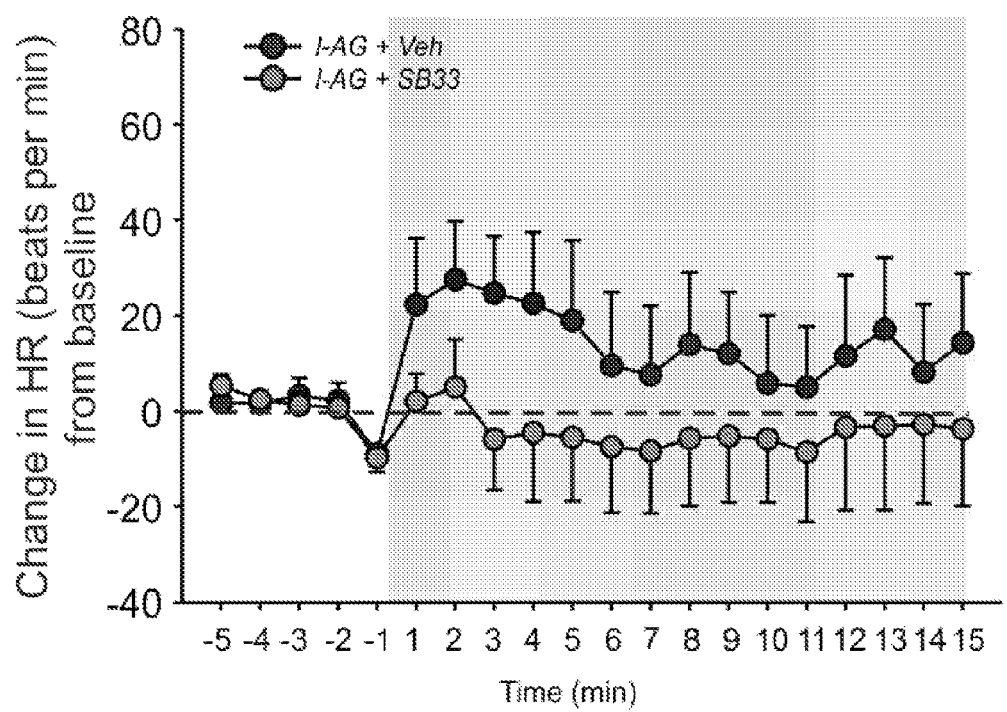
FIG. 16 shows heart rate after sodium lactate (NaLac) challenge in panic prone rats pre-treated with systemic injections of SB334867 (SB33).
Figure 17:
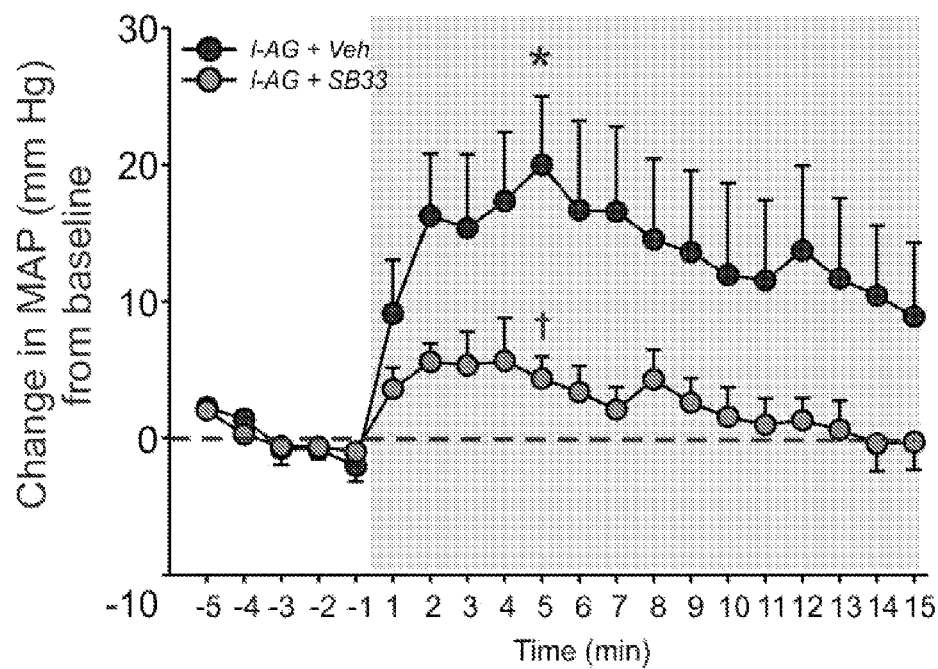
FIG. 17 shows mean arterial pressure after sodium lactate (NaLac) challenge in panic prone rats pre-treated with systemic injections of SB334867 (SB33).

Systemically injecting SB334867 i.p. into panic-prone rats prior to NaLac challenges attenuated anxiety-like responses [FIG. 14, decreased time spent in center of open field; n=8, 4, 6; one outlier detected in veh NaLac treated rats (Grubb's test, z value=1.89, $p<0.05$), treatment effect, Levene's test for homogeneity revealed unequal variance, $F_{(2,15)}=9.6$, $p=0.002$ so a nonparametric a Kruskal-Wallis ANOVA/Mann-whitney U-test was $F_{(2)}=7.4$, $p=0.025$) and NaLac induced increases in and heart rate (FIG. 16, HR, n=5, 5; drug×time effect $F_{(19,152)}=0.6$, $p=0.873$), and mean arterial blood pressure (FIG. 17, MAP, n=5, 5; drug×time effect $F_{(19,152)}=2.7$, p=0.001). No change was detected in general locomotor activity (FIG. 15, n=5, 5; drug×time effect $F_{(7,56)}$=0.9, p=0.480). Baseline analyses revealed significant difference in activity ($t_{(4)}$=−2.9, p=0.043), but not for HR ($t_{(4)}$=−0.04, p=0.972) or MAP ($t_{(4)}$=−0.12, p=0.908). Histology verified that all minipump cannulae were in the DMH region.

Example

Systemic SB408124 in Panic-Prone Rats Prior to Lactate Challenge

Adult male Sprague-Dawley rats were anesthetized and surgically implanted with telemetrical probes to measure cardiovascular activity. After a 3 day recovery, rats were anaesthetized and had osmotic minipumps (previously filled with 1-AG) stereotaxically implanted unilaterally into the DMH. 5 days later, in a counterbalanced design, half of these rats received a prior intraperitoneal (i.p.) injection of an ORX1 R antagonist [30 mg/kg SB408124, cat. no. 1963, Tocris, in 0.2 ml/100 g volume DMSO, n=4] or vehicle (0.2 ml/100 g volume DMSO, n=6) 30 min prior lactate challenge.

Prior i.p. injections of SB408124, but not vehicle, attenuated lactate induced tachycardia responses in panic-prone (1-AG treated) rats [HR (drug×time $F_{(19,114)}$=3.7, p=0.001); MAP (drug×time $F_{(19,114)}$=0.9, p=0.629); SI ($F_{(3,20)}$=2.1, p=0.133) (see FIGS. 19-21)]. None of the baseline analyses were significantly different between groups [Activity, $t_{(3)}$=−2.5, p=0.101; MAP, $t_{(3)}$=−1.1, p=0.345; HR, $t_{(3)}$=−0.3, p=0.804]. Histology verified that all minipump cannulae were in the DMH region.

Example

Systemic SB334867 on Baseline Behavior and Cardiovascular Activity in Control Rats Adult male Sprague-Dawley rats were anesthetized and surgically implanted with telemetrical probes to measure cardiovascular activity prior to and during lactate infusions. After a 3 day recovery, in a counterbalanced design, half of these rats received a prior intraperitoneal (i.p.) injection of an ORX1R antagonist [30 mg/kg SB334867, cat. no. 1960, Tocris, in 0.2 ml/100 g volume DMSO, n=7] or vehicle (0.2 ml/100 g volume DMSO, n=7). Cardiovascular activity and SI tests were monitored 30 min following injection at similar time points.

Administering same dose of SB334867 to control rats had no effect on HR (drug×time $F_{(19,228)}$=0.8, p=0.691), MAP (drug×time $F_{(19,228)}$=0.001, p=0.974) or SI duration ($F_{(2,18)}$=0.5, p=0.604) 30 min following injections (monitored for 20 min starting at the min post injection time point).

Example

Experiment 8. 1-AG and 1-AG+NaLac Effects on Unconditioned Defensive Burying-Associated Behaviors On day 1 adult male Sprague-Dawley rats (n=3/group) were anaesthetized and had osmotic minipumps (previously filled with 1-AG) stereotaxically implanted unilaterally into the DMH/PeF. Prior to testing, rats either received an i.p. injection of the ORX1R antagonist, SB334867 [30 mg/kg, cat. no. 1960, Tocris, in 0.2 ml/100 g volume DMSO, n=3], or vehicle (0.2 ml/100 g volume DMSO, n=6) 30 min prior challenge infusion. The SB334867+1-AG group of rats (n=3) and 3 of the vehicle+1-AG rats were given an i.v. infusion of NaLac, whereas the remaining vehicle+1-AG group were infused with saline. Immediately following the offset of the i.v. infusion, rats were placed individually in the test cage away from the shock probe (near short dimension side of cage that did not have probe) and 10 min sessions were videotaped for later assessment of defensive burying behavior. Time spent burying, in proximity of probe, grooming (30.5 cm width×61 cm length cage was divided into two 30.5×30.5 areas; one near probe and one distal from probe) and freezing as well as number of center line crossings were assessed. Behavioral assessments were made using software (ODLog Macropod Software for Windows, version 2.5.2) with different keystrokes coupled to each defensive behavior to accurately measure incidence and duration of each.

All rats received explored the probe and received a shock (verified by contact with probe+startle response) within 45 sec of 5 min test. Assessment of defensive burying associated behaviors revealed that, compared to saline infused controls, 1-AG+NaLac+Veh treated rats spent over half of the 5 min DB test immobile or "freezing" ($F_{(2,6)}$=7.9, p=0.002), which was completely blocked in the 1-AG+NaLac group treated with the SB334867 compound (see FIG. 22a). An interesting finding was that, compared to the 1-AG+NaLac rats injected with SB334867, the 1-AG+sal and 1-AG+NaLac rats treated with vehicle spent little to no time burying during the test ($F_{(2,6)}$=12.1, p=0.008). No differences were detected in time spent near probe ($F_{(2,6)}$=2.3, p=0.182), rearing ($F_{(2,6)}$=1.2, p=0.360), or grooming ($F_{(2,6)}$=3.1, p=0.112).

Example

Experiment 9. ORX1 Receptor Antagonist into the Bed Nucleus of the Stria Terminalis (BNST) of 1-AG+NaLac-Treated Rats Rats (n=5/group in a crossover design) were treated with 1-AG into the DMH/PeF and 5 days postpump received unilateral injections of SB334867 (300 pmoles/100 nl of DMSO vehicle) or DMSO vehicle directed at the BNST [using a 33 gauge injector (ck no. C315I, Plastics One), which extended 1 mm past the 24 gauge cannula (cat. no. C315G, Plastics One)] 30 min prior to receiving i.v. infusions of 0.5 M sodium lactate. Stereotaxic coordinates relative to bregma for the BNST, using a 10° angle from the vertical plane with the incisor bar set at +5 mm were: Anterior +1.0 mm, Lateral +2.5 mm and Ventral −7.0 mm. An SI test was conducted immediately following the offset of the lactate challenge. 48 h was allowed between randomized injections.

Unilateral injections of an ORX1 receptor antagonist (i.e., SB334867, 300 pmoles/100 nl of DMSO vehicle) into the BNST of 1-AG treated rats prior to the lactate challenge reduced the duration of SI as compared to DMSO vehicle injected rats ($t_{(4)}$=6.9, p=0.0002, n=5/crossover design, see FIG. 22c). Infusion sites for 1-AG into the DMH/PeF and vehicle and SB334867 injection sites into the BNST were confirmed.

Example

1-AG Effects on Unconditioned Acoustic

Example

Experiment 10. 1-AG Effects on Unconditioned Acoustic Startle

In experiment 10, rats (n=8/group) were made panic vulnerable with 1-AG. An acoustic startle reflex was tested the day prior to receiving the 1-AG pump surgeries and 5 days following the onset of the 1-AG pump infusions.

Adult male Sprague-Dawley rats (n=8/group) were anaesthetized and had osmotic minipumps (previously filled with 1-AG) stereotaxically implanted unilaterally into the DMH/PeF. An acoustic startle reflex was tested the day prior to receiving the 1-AG pump surgeries and 5 days following the onset of the I-AG pump infusions.

Figure 23:
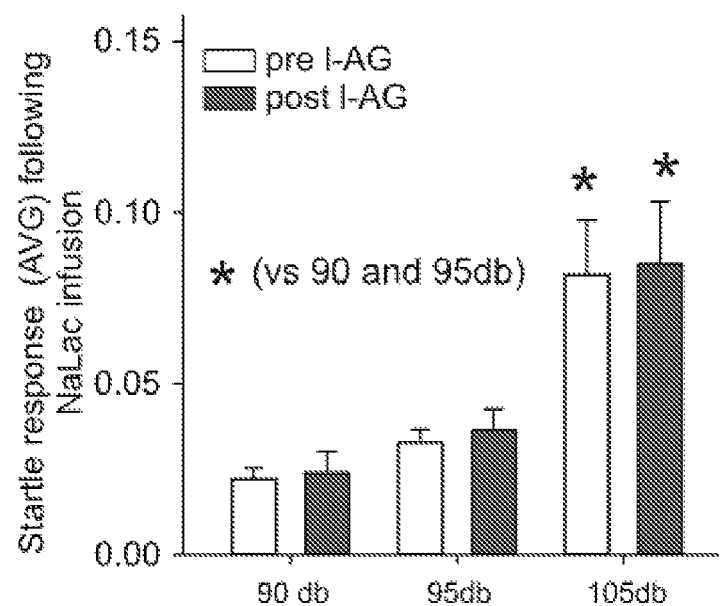
FIG. 23 shows acoustic startle responses in response to 1-AG infusions into the DMH/PeF.

Unconditioned acoustic startle responses were not altered by 1-AG infusions into the DMH/PeF when comparing responses prior to and after 1-AG infusions (FIG. 23) [there was an increase in the acoustic startle response in both groups due to increases in decibel intensity $F_{(2,28)}=29.8$, p=0.001; but no overall I-AG effect $F_{(1,14)}=0.1$, p=0.810; or 1-AG× decibel intensity interaction $F_{(2,28)}=0.01$, p=0.993]. Histology verified that all minipump cannulae were in the DMH/PeF region. These results indicate that panic-like and anxiety-like responses elicited by infusions of 1-AG into the DMH is not due to a non-specific increase in arousal as there are no changes noted in baseline unconditioned acoustic startle responses, a finding that is also noted in subjects with panic disorder.

Example

Experiment 11. Activation of Orexin System is a Component of $CO_2$ Mediated Anxiety and Hypertension But Not Bradycardia All experiments were conducted on adult male Sprague-Dawley rats (300-350 g) purchased from Harlan Laboratories (Indianapolis, Ind., USA) and were housed individually in plastic cages under standard environmental conditions (22° C.; 12/12 light/dark cycle; lights on at 7:00 A.M.) for 7-10 days prior to the surgical manipulations. Food and water were provided ad libitum. Animal care procedures were conducted in accordance with the NIH Guidelines for the Care and Use of Laboratory Animals (NIH Publication no. 80-23) revised 1996 and the guidelines of the IUPUI Institutional Animal Care and Use Committee.

Prior to surgery, rats were anesthetised with a nose cone connected to an isoflurane system (MGX Research Machine; Vetamic, Rossville Ind., USA) during the surgery. All rats were fitted with femoral arterial catheters for measurement of mean arterial blood pressure (MAP) and heart rate (HR) as previously described (Shekhar et al., 1996). Briefly, cardiovascular responses were measured by a femoral arterial line connected to a telemetric probe that contained a pressure transducer [Cat. no. C50-PXT, Data Sciences International (DSI), St. Paul, Minn., USA]. DSI dataquest software was used to monitor and record MAP and HR. For the duration of each experiment, MAP and HR were recorded continuously in freely moving conscious rats. Data were analyzed during the period 5 min prior to, 5 min during, and 5 min following the gas challenges. The data reported are changes in HR and MAP, expressed in 1 min bins, relative to the average of the baseline measurement (t−5 min to t−1 min) from each rat.

Flow cages (12 in. width×12 in. height×24 in. length) were custom built using Plexiglas®. When the lid of the cage was latched, gases could only enter the cage through an inlet connector (for the gas infusion) and could only exit the cage through an outlet connector. The gas flow into the cages was controlled using a 2-stage regulator (Praxair, Inc., Danbury, Conn., USA) at a pressure of 0.6 Bar. The consistency of the rate of $CO_2$ delivery was validated using state-of-the-art infrared $CO_2$ ($ProCO_2$) and electrochemical $O_2$ ($ProO_2$) sensors in Experiment 12.

On day 1, rats (n=3/group) were selected from their home cages and placed into experimental cages containing atmospheric air. All rats had infusions of the following: 1) 5 min infusion of premixed atmospheric gas (<1% $CO_2$, 21% $O_2$, 79% $N_2$: Praxair, Inc.) for baseline measurements, then 2) either the premixed atmospheric control gas (<1% $CO_2$, 21% $O_2$, 79% $N_2$) or premixed experimental normoxic, hypercarbic gas (20% $CO_2$, 21% $O_2$, 59% $N_2$: Praxair) for 5 min (note: for control rats the atmospheric gas was turned off and back on again at the beginning and end of this infusion to be identical to the manipulations for the hypercarbic gas challenge), and finally, 3) 5 min infusion of atmospheric gas. Fecal pellets were counted in cages at the end of gas challenges. In order to assess anxiety-like behavioural responses following exposure to hypercarbic gas, rats were immediately transferred to an adjacent room and place in the center square of an open-field box for a 5 min test. On day 2, the experiment was repeated, but the treatments were reversed for each rat. For instance, rats that received atmospheric gas challenge on day 1 received the hypercapnic gas challenge on day 2.

The open-field arena covered an area of 90 cm×90 cm, with 40 cm high walls. The open-field arena was divided into a 6×6 grid of equally-sized squares using black tape (36 total squares) with 4 squares forming the center; 12 squares forming the middle perimeter; and 20 squares forming the outer perimeter. The test started by placing a rat in the center. The behavior of each rat in the open-field arena was recorded on video and scored afterwards by an observer (PLJ) blind to the experimental treatment of each rat. Time spent in each region of the open-field was recorded. In addition, locomotor activity was assessed by counting the number of times the rat's entire body (excluding tail) completely crossed into another square.

Infusion of premixed gases, either atmospheric air (<1% $CO_2$, 21% $O_2$, 79% $N_2$) or normoxic, hypercarbic gas (20% $CO_2$, 21% $O_2$, 59% $N_2$) (Praxair Espana, Madrid, Spain), began 1 min after placement of rats (n=7/group) in the cages and continued for 5 min. At that time the gas flow was terminated and cages were opened to allow rapid equilibration with atmospheric air. Rats were left in the cages for an additional 5 min and then were transferred to their original home cages.

Ninety min following the initiation of treatment, rats were anesthetized with an overdose of sodium pentobarbital (40 mg, i.p.) then perfused transcardially with 0.05 M phosphate buffered saline (PBS; 250 ml), followed by 0.1 M sodium phosphate buffer (PB; 250 ml) containing 4% paraformaldehyde (PFA) and 3% sucrose. Brains were removed and post-fixed for 24 h in the same fixative, rinsed for 24 h in 0.1 M PB, then placed in cryoprotectant (30% sucrose in 0.1 M PB) for an additional 4-5 days. To maintain a consistent plane for coronal sections, brains were placed in a rat brain matrix (ASI instruments, Model No. RBM-4000C, Warren Mich., USA) and cut with a razor blade at the caudal border of the mammillary bodies. Brains were frozen in cooled liquid isopentane made by immersing a plastic vessel containing isopentane into a dewar flask containing liquid nitrogen. Serial coronal sections (30 µm) were cut using a cryostat and were immediately placed in cryoprotectant consisting of 27% ethylene glycol and 16% glycerol in 0.05 M PB to yield six alternate sets of sections. Sections were stored at ~20° C. until immunohistochemical processing. All solutions had a pH of 7.4.

Double immunostaining for c-Fos protein and ORX was accomplished with sequential immunohistochemical procedures using 1) primary antibodies directed against c-Fos (rabbit anti-c-Fos polyclonal antibody, Cat. no. sc-52, Ab-5, Santa Cruz Biotech., Santa Cruz, Calif., USA; diluted 1:10,000)

then 2) primary antibodies directed against ORX-A (rabbit anti-ORX-A-polyclonal, affinity-purified antibody, Cat. no. H-003-30, Phoenix Pharmaceuticals, Burlingame, Calif., USA; diluted 1:10,000). All brain sections were immunostained in a single immunohistochemical run, rather than in batches, with large volume incubations to limit variability in the quality of immunohistochemical staining among brain sections.

Free-floating sections were washed in 0.05 M PBS for 30 min, then incubated in 1% $H_2O_2$ in PBS for 20 min. Sections were then washed 10 min in PBS and 20 min in PBS with 0.3% Triton X-100 (PBST). Sections were then incubated 12-16 hr in PBST with primary antibody solution at room temperature. After a 30 min wash in PBST, sections were incubated in biotinylated goat anti-rabbit IgG (c-Fos, ORX-A; Cat .no. BA-1000; Vector Laboratories, Burlingame, Calif., USA; diluted 1:500). Sections were washed again for 30 min in PBST then incubated 1.5 hr in an avidin-biotin complex provided in a standard Vector Elite kit (c-Fos, ORX-A, Cat no. PK-6100, Vector Laboratories; diluted 1:500). Substrates for chromogen reactions were SG (c-Fos; SK-4700, Vector Laboratories) or 0.01% 3,3'-diaminobenzidine tetrahydrochloride (ORX-A; DAB) (Cat. no. D-5637, Sigma-Aldrich, Poole, UK) in PBS containing 0.003% $H_2O_2$, pH 7.4. Substrate reactions were run for 20 min for c-Fos and 10 min for ORX-A. All sections were mounted on clean glass slides, dried overnight, dehydrated and mounted with cover slips using DPX mounting medium (BDH Laboratory Supplies, Poole, U.K.). All washes and incubations were done in 12-well polystyrene plates with low frequency shaking on an orbital shaker.

Selection of anatomical levels for analysis of c-Fos/ORX-A-immunostained cells was conducted with reference to illustrations from a rat brain stereotaxic atlas (Paxinos and Watson, 1997). Selection of anatomical levels was also done in reference to major anatomical landmarks including white matter tracts and the ventricular systems. Specifically, darkfield contrast [i.e., using a 1.6× Leica phase contrast Plan objective and Leica binocular microscope (model DMLB, Leica Mikroskopie and Systeme GmbH, Wetzler, Germany) with a darkfield condenser] was used to visualise white matter tracts (e.g., the formix and optic tracts) and ventricular systems (e.g., lateral, $3^{rd}$ ventricles) that aided in selection of appropriate coronal levels with reference to illustrations in a standard stereotaxic atlas of the rat brain (Paxinos and Watson, 1997). The numbers of c-Fos/ORX-A-ir neurons were counted in the entire field of view at 400× magnification (i.e., 10× eyepiece and 40× Plan objective) for each brain region. The area of the DMH/PeF where single ORX-A-ir neurons and double c-Fos/ORX-ir neurons was counted was roughly square in dimension with the corners being the mammillothalamic tract, the formix, the top of the $3^{rd}$ ventricle and a point located halfway down the $3^{rd}$ ventricle (immediately medial from the formix). The DMH/PeF, as described, is particularly sensitive to BMI-induced cardioexcitatory response. All single ORX-A-ir neurons and double c-Fos/ORX-ir neurons counted that were lateral to the DMH/PeF area were considered to be in the LH region. All cell counts were done by an observer that was blind to the experimental treatment of each animal.

Photomicrographs were obtained using a brightfield microscope using N Plan 5×, 10×, 40× and 63× objective lenses (Leica binocular microscope, model DMLB), an Insight digital camera (Diagnostics Instruments Inc., Sterling Heights, Mich., USA) and SPOT 3.5.5 for Windows digital imaging software (Silicon Graphics, Mountain View, Calif., USA). Photographic plates were prepared in CorelDraw 11.633 for Windows.

Figure 24:
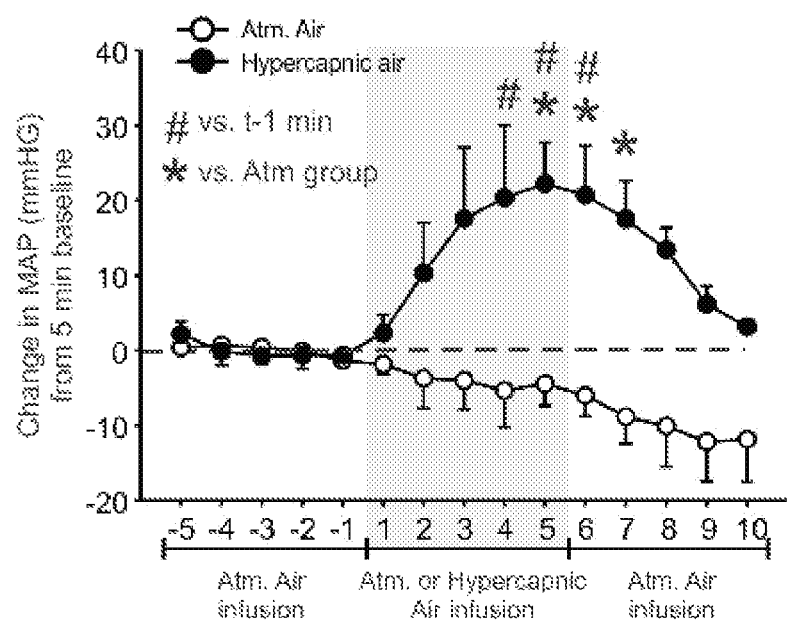
FIG. 24 shows mean arterial pressure after infusion of hypercapnic or atmospheric air.
Figure 25:
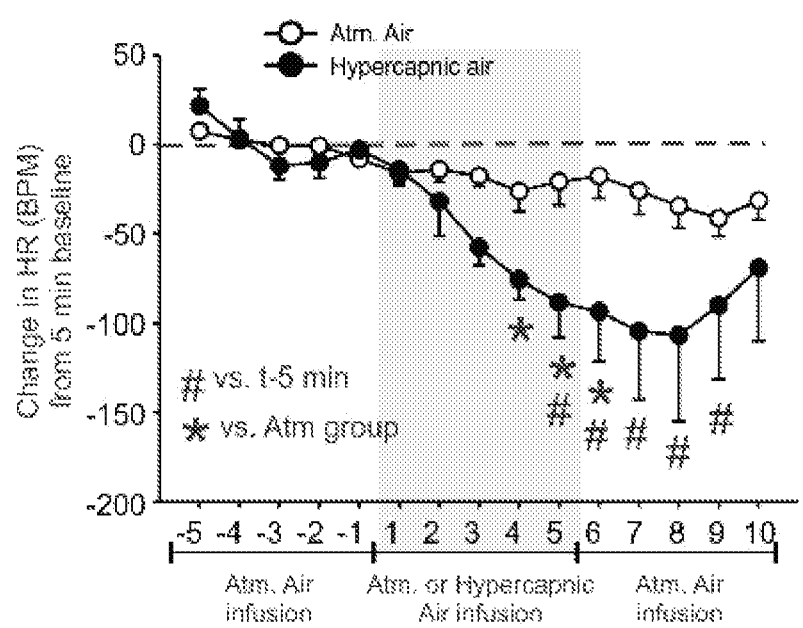
FIG. 25 shows heart rate after infusion of hypercapnic or atmospheric air.
Figure 26:
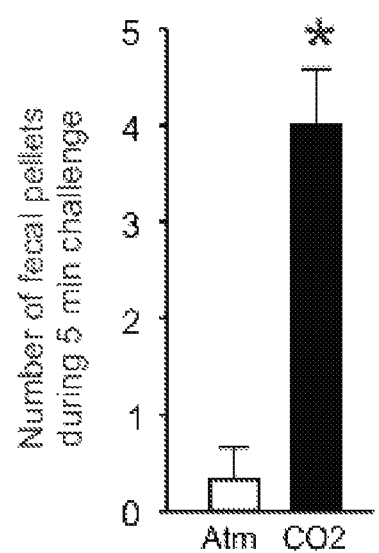
FIG. 26 shows number of fecal pellets after infusion of hypercapnic ($CO_2$) or atmospheric (Atm) air.

Infusion of hypercarbic, but not atmospheric, gas increased MAP (gas infusion×time interaction, $F_{(14,56)}$=6.4, P=0.0001; gas infusion effect, $F_{(1,4)}$=11.0, P=0.029; $CO_2$ group within group time effect, $F_{(14,30)}$=3.3, P=0.003, FIG. 24) and decreased HR (gas infusion×time interaction $F_{(14,56)}$=2.4, P=0.011; $CO_2$ group within group time effect $F_{(14,30)}$=3.1, P=0.005, FIG. 25) without altering locomotor activity (gas infusion×time interaction $F_{(1,4)}$=2.5, P=0.200). A 5 min atmospheric gas challenge did not alter MAP (FIG. 24), HR (FIG. 25) or locomotor responses relative to the 5 min baseline. Rats exposed to hypercarbic gas also had increased numbers of fecal pellets post challenge, compared to atmospheric gas challenged controls ($t_{(2)}$=−4.2, P=0.027, FIG. 26). No significant differences in baseline MAP, HR or activity (over 5 min initial atmospheric gas exposure prior to challenge with experimental gases) were noted between treatment groups.

Open-Field Test

Figure 27:
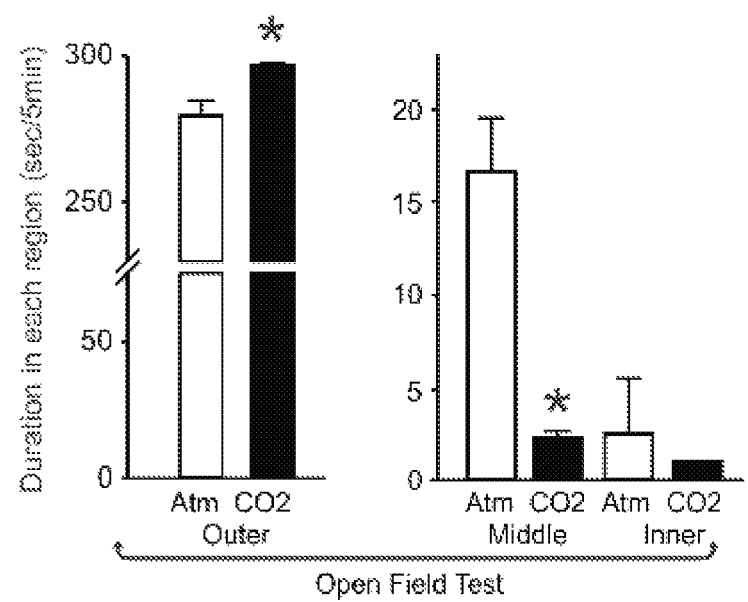
FIG. 27 shows open field test results after infusion of hypercapnic ($CO_2$) or atmospheric (Atm) air.

Compared to atmospheric gas-challenged rats, hypercarbic gas-challenged rats spent less time in the middle perimeter (thd (2)=5.4, P=0.016) and more time in the outer perimeter ($t_{(2)}$=−3.5, P=0.036) of the open-field (FIG. 27). No difference was noted between groups for the time spent in the center ($t_{(2)}$=1.0, P=0.211) of the open-field.

Example

Experiment 12 Effects of Hypercarbic Gas on Hypothalamic ORX mRNA Expression

Adult male rats were housed as stated in the previous Example. On the day of the experiment, rats were placed in flow cages (12 in. width×12 in. height×24 in. length) and infusion of premixed gases, either atmospheric air (<1% $CO_2$, 21% $O_2$, 79% $N_2$) or normoxic, hypercarbic gas (20% $CO_2$, 21% $O_2$, 59% $N_2$) began 1 min after placement of rats (n=8/group) in the cages and continued for 5 min. At that time the gas flow was terminated; the cages were opened; and rats were transferred to their original home cages. Thirty min following the gas challenge rats were anaesthetized and decapitated. Brains were removed and flash frozen in isopentane pre-cooled on dry ice. Brains were stored at −80° C. till sectioned.

All equipment and working surfaces were kept RNase-free during dissection of the regions of interest. Serial coronal brain sections (300 μm thickness) were cut using a cryostat (Leica) and placed on pre-cooled glass slides. The regions encompassing the orexin population of neurons (DMH and LH) were dissected from two adjacent coronal sections between −2.8 to −3.4 mm bregma using tissue micropunches (inside diameter=1 mm) at specific locations. Tissues from the micropunches were placed directly into a lysis buffer (SurePrep RNA/DNA/Protein Purification Kit, Fisher Scientific, Hampton, N.H., USA) and stored at −80° C. until use. Total RNA was isolated using the SurePrep RNA/DNA/Protein Purification kit (Fisher Scientific, Cat. no. BP2802-50) using the manufacturer's protocol. Concentrations of samples were determined on a Nanodrop 1000 system (Thermo Scientific, Waltham, Mass., USA), and stored at −80° C. until conversion into cDNA. All total RNA samples were diluted to the same concentration in nuclease-free water (Ambion, Austin, Tex., USA, Cat no. AM9938) and then converted to cDNA with a High Capacity cDNA Reverse Transcription kit (Applied Biosystems, Foster City, Calif., USA, cat. no. 4368814) in a Mastercycler PCR machine (Eppendorf Inc., Hamburg, Germany) using the manufacturer's protocol. RT-PCR gene assays for prepro-ORX (Applied Biosystems, Cat. no. Rn00565995) and beta actin (Applied Biosystems, Cat. no. 4352931E) were performed in triplicate using 3.5 ng cDNA for each sample. RT-PCR assays were performed in a 7900HT Fast Real-Time PCR System (Applied Biosystems) and relative quantity of mRNA was calculated by delta-deltaCt method using SDS v 2.3 software (Applied Biosystems) using beta actin expression as the normalization factor.

Figure 28:
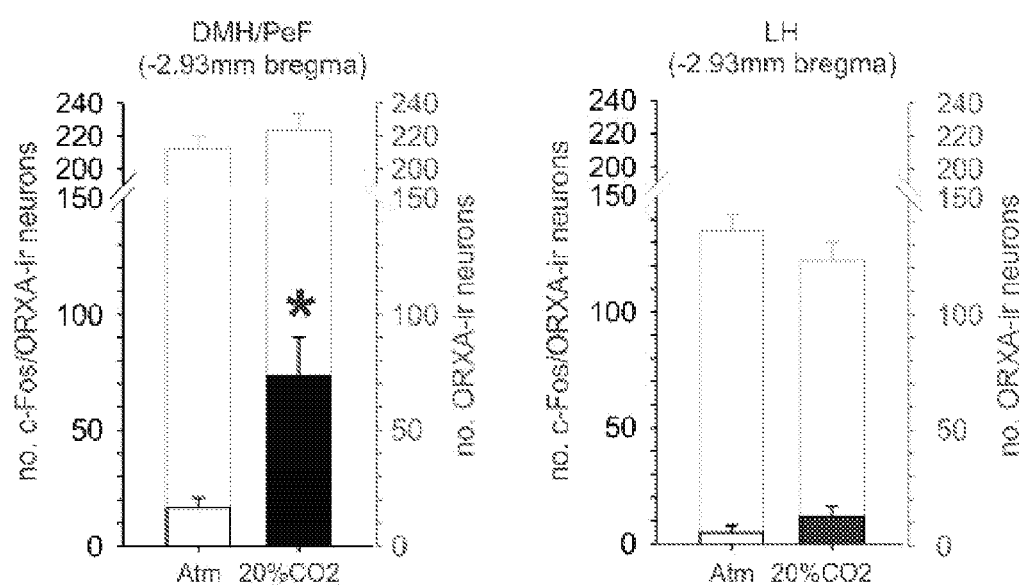
FIG. 28 shows number of c-Fos/orexinA immunoreactive (c-Fos/ORXA-ir) neurons in DMH/PeF and LH hypothalamic regions at −2.93 mm to Bregma following exposure to hypercapnic or atmospheric air.
Figure 29:
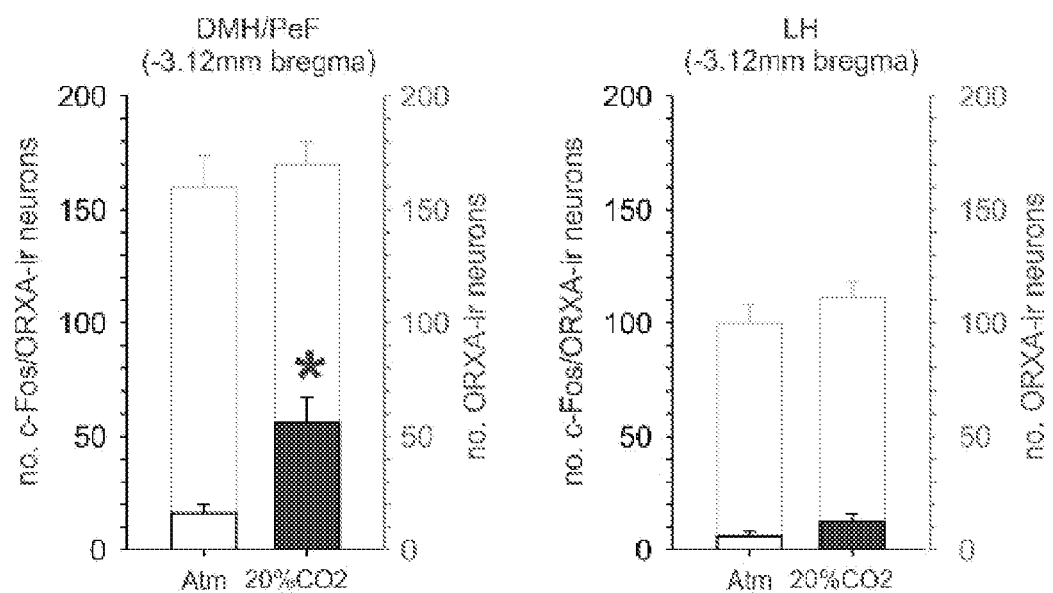
FIG. 29 shows number of c-Fos/orexinA immunoreactive (c-Fos/ORXA-ir) neurons in DMH/PeF and LH hypothalamic regions at −3.12 mm to Bregma following exposure to hypercapnic ($CO_2$) or atmospheric (Atm) air.

Rats exposed to hypercarbic gas had greater numbers of c-Fos/ORXA-ir neurons in the DMH/PeF, but not LH, as compared to rats exposed to atmospheric air DMH/PeF (−2.94 mm bregma: gas infusion×region interaction, $F_{(1,12)}=10.5$, P=0.007; −3.12 mm bregma: gas infusion×region interaction, $F_{(1,12)}=11.1$, P=0.006). The increase in c-Fos/ORXA-ir neurons occurred in the DMH/PeF (−2.94 mm bregma: $F_{(1,12)}=11.2$, P=0.006; −3.12 mm bregma: $F_{(1,12)}=12.5$, P=0.004, FIG. 29), but no effect was observed in the LH (−2.94 mm bregma: $F_{(1,12)}=1.8$, P=0.206 FIG. 28; −3.12 mm bregma: $F_{(1,12)}=2.4$, P=0.145, FIG. 1c). There was no significant effect of gas exposure (−2.94 mm bregma: gas infusion×region interaction, $F_{(1,12)}=2.9$, P=0.114; −3.12 mm bregma: gas infusion×region interaction, $F_{(1,12)}=0.02$, P=0.901) on total numbers of ORXA-ir neurons in either the DMH/PeF (−2.94 mm bregma: $F_{(1,12)}=0.8$, P=0.389 FIG. 28; −3.12 mm bregma: $F_{(1,12)}=0.3$, P=0.564, FIG. 29) or LH (−2.94 mm bregma: $F_{(1,12)}=1.4$, P=0.266 FIG. 28; −3.12 mm bregma: $F_{(1,12)}=1.1$, P=0.304, FIG. 29).

Hypercarbic Gas Exposure

In Experiment 12, the effects of this 5 min 20% $CO_2$/normoxic gas challenge on $O_2$ and $CO_2$ concentrations in ambient air of experimental cages have previously been described. Concentrations of $O_2$ remain at 21% throughout the gas infusion in the control and experimental cages. The $CO_2$ concentration remains constant at <1. % in the control cage during exposure of rats to atmospheric air (<1% $CO_2$/21% $O_2$/79% $N_2$). Infusion of the premixed normoxic, hypercarbic gas (20% $CO_2$/21% $O_2$/59% $N_2$) results in a rapid increase in $CO_2$ concentration from <1% $CO_2$ up to 20% $CO_2$ at the 5 min time point. After terminating gas infusion and opening the cages the concentration of $CO_2$ rapidly decreases from 20% $CO_2$ to <2.5% $CO_2$ during the following 5 min.

Example

Effects of an ORX1 Antagonist on Hypercarbic Gas-Induced Changes in Behavior and Cardiovascular Activity All rats received hypercarbic gas infusions as described in detail in Experiment 11. However, 30 min prior to the hypercarbic gas challenge rats were injected with vehicle (0.2 ml/100 g volume dimethyl sulfoxide (DMSO)) or a dose of an ORX1 receptor antagonist (30 mg/kg SB334867, Tocris Bioscience, Bristol, UK, in 0.2 ml/100 g volume DMSO, i.p.) that blocks stress-induced anxiety-like behavior and panic-associated cardioexcitatory responses without inducing somnolence. This drug crosses the blood-brain barrier and does not alter MAP, HR or locomotor activity in control rats. Blood pressure, heart rate, locomotor activity, number of fecal pellets and anxiety-like behavior were assessed as described in Experiment 11.

Figure 30:
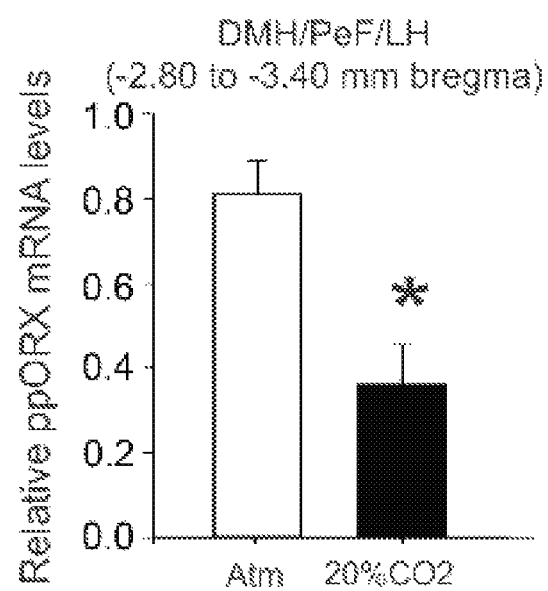
FIG. 30 shows expression level of prepro-orexin mRNA in combined DMH/Pe/LH hypothalamic regions following exposure to hypercapnic ($CO_2$) or atmospheric (Atm) air.

Compared to rats exposed to atmospheric gas, rats exposed to hypercarbic gas had reduced expression of ppORX mRNA in the combined DMH/PeF/LH ($t_{(14)}=3.6$, p=0.0028) (FIG. 30).

Statistical Analyses of Cardiovascular Responses and Open-Field Behavior.

Dependent variables for analyses of cardiovascular responses (HR, MAP) and locomotor activity were analysed using a one-way ANOVA with repeated measures, using gas infusion as the between-subjects factor and time as a within-subjects factor. Dependent variables for the number of fecal pellets and open-field anxiety test (i.e., time spent in each section, line crossings) were analysed using a one-way ANOVA with gas infusion in Experiment 11 and drug treatment in Experiment 12 as the between-subjects factors. In the presence of significant main effects or main effect×time interactions, Fisher's Least Significant Difference (LSD) or paired t-tests were used for post-hoc pairwise comparisons since each rat received both atmospheric and hypercarbic gas infusions (Experiment 11) or vehicle+hypercarbic gas or SB334867+hypercarbic gas (Experiment 12) on different days. Within-subjects comparisons were also made on the MAP and HR measures using a Dunnett's test for multiple comparisons with a single control using the 5 Min baseline measurement as the control. The alpha level was set at 0.05 in all cases.

All statistical analyses were carried out using SYSTAT 5.02 (SYSTAT Inc., San Jose, Calif., USA) and SPSS14.0 (SPSS Inc., Chicago, Ill., USA), and all graphs were generated using SigmaPlot 2001 (SPSS Inc.) and an illustration program (CorelDraw 11.633 for Windows, Viglen Ltd., Alperton, UK).

Figure 31:
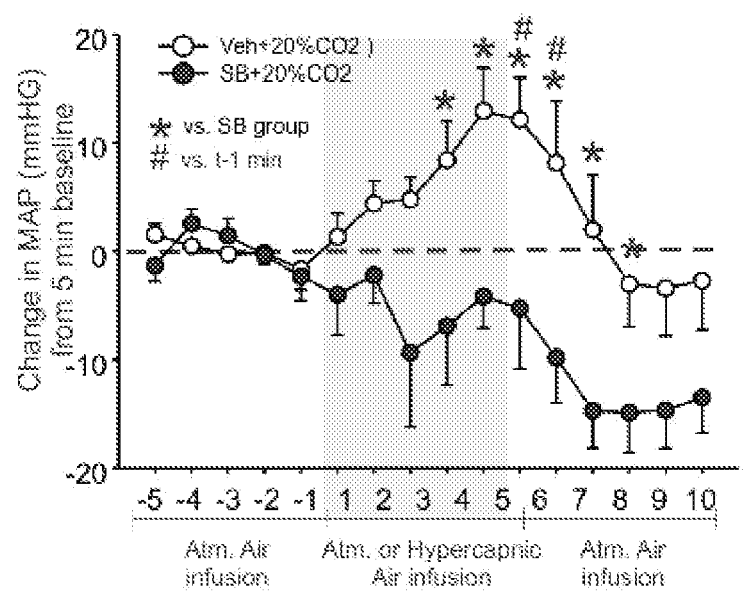
FIG. 31 shows mean arterial pressure during infusion of hypercapnic and atmospheric air in rats pre-treated with SB334867 or vehicle.
Figure 32:
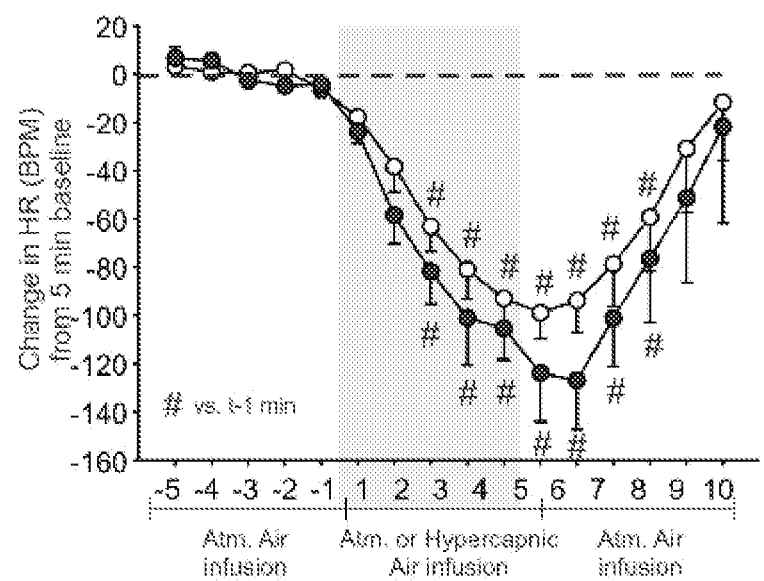
FIG. 32 shows heart rate during infusion of hypercapnic and atmospheric air in rats pre-treated with SB334867 or vehicle.
Figure 33:
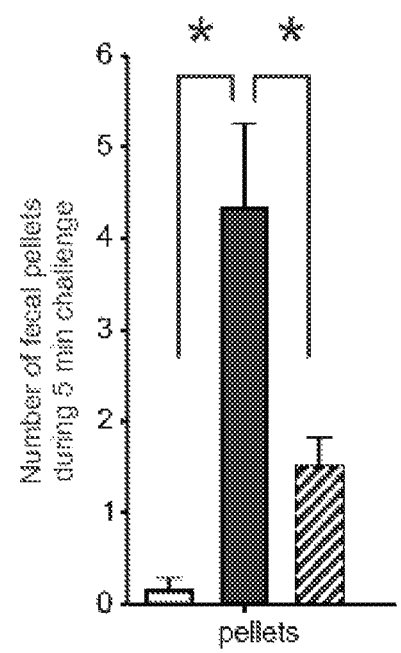
FIG. 33 shows number of fecal pellets during infusion of atmospheric air and during infusion of hypercapnic air in rats pre-treated with vehicle (solid bar) or SB 334867 (hatched bar).

Prior i.p. injections of SB334867, but not vehicle, attenuated hypercarbic gas-induced changes in MAP (drug×time interaction $F_{(14,182)}=6.4$, P=0.0001; drug treatment effect $F_{(1,13)}=11.0$, P=0.029; the veh/$CO_2$, but not SB/$CO_2$, group had a within group time effect $F_{(14,105)}=2.6$, P=0.003, FIG. 31), but unexpectedly had no effect on hypercarbic gas-induced bradycardia [drug×time interaction $F_{(14,182)}=0.5$, P=0.931; drug treatment effect $F_{(1,13)}=1.0$, P=0.346, with both the veh/$CO_2$ ($F_{(14,105)}=9.8$, P<0.001) and SB/$CO_2$ ($F_{(14,90)}=8.9$, P<0.001) group having a within group time effect, FIGS. 31-32]. Neither the vehicle nor SB334867 treated rats had a change in locomotor responses over time prior to, during or after hypercarbic gas. Vehicle-treated rats exposed to hypercarbic gas had increased numbers of fecal pellets, relative to atmospheric gas challenged control rats, which was attenuated by SB334867 (SB/$CO_2$ group: $F_{(2,21)}=5.6$, P=0.012, FIG. 33). No significant differences in baseline MAP or HR (over 5 min initial atmospheric gas challenge prior to experimental gases) were noted between treatment groups. However, rats pretreated with SB334867 did have higher locomotor activity prior to hypercarbic gas infusion than the vehicle-treated rats ($t_{(6)}=-2.6$, P=0.039). The hypercarbic gas-treated group only had an n of 7 due to a malfunctioning telemetry probe sending MAP and HR readings outside of the physiological range on the last test day.

Open-Field Test

Figure 34:
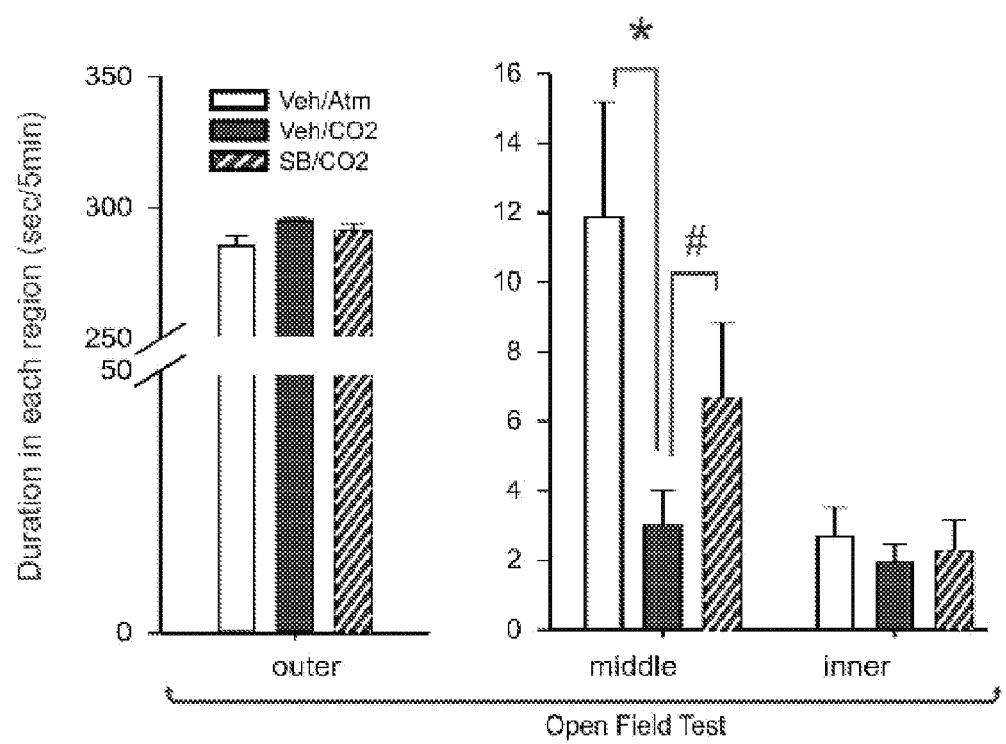
FIG. 34 shows open field test results after infusion of atmospheric air (Atm) or hypercapnic air ($CO_2$) in rats pre-terated with vehicle (veh) or SB 334867 (SB).

Vehicle-treated rats exposed to hypercarbic gas spent less time in the middle perimeter area than vehicle-treated rats exposed to atmospheric air ($F_{(2,21)}=3.6$, P=0.045, FIG. 34). Although approaching significance with a Fisher's LSD post hoc test (protected by the previous ANOVA result) comparing the Veh/$CO_2$ to the SB/$CO_2$ (p=0.056), comparing the Veh/$CO_2$ group to the SB/$CO_2$ group reveals that the SB/$CO_2$ group spent significantly more time in the middle perimeter region than the Veh/$CO_2$ group ($t_{(7)}=-2.7$, p=0.016). No differences in the time spent in the center ($F_{(2,21)}=0.2$, p=0.790) or outer perimeter ($F_{(2,21)}=0.2$, P=0.085) regions were noted.

Example c-Fos/ORX Responses to Anxiogenic Drugs c-Fos expression was examined, in combination with specific neurochemical markers, in the DMH/PeF region that may be involved in regulating the autonomic and behavioral responses to sodium lactate in intra-DMH/PeF 1-AG-treated rats.

Adult male Wistar rats (250-300 g; B&K Universal, Hull, UK) were acclimatized to the animal facility for 1 week in group housing (four/cage), then single-housed on a 14:10-h light/dark cycle (lights on at 05:00 h) and habituated to the experimental room (36-48 h) before the experiment. Food and water were provided ad libitum. Injections were performed using a completely randomized experimental design utilizing 16 rats each day on 2 separate days (during the rats' inactive phase).

Time-matched groups of rats were injected between 09:00 and 17:00 h. Rats were injected i.p. with either saline vehicle (n=8), the 5-HT2A/2C receptor agonist mCPP (Sigma, Dorset, UK; 5 mg/kg; n=6), the adenosine receptor antagonist caffeine (Fluka, Dorset, UK; 50 mg/kg; n=6), the 2-adrenoreceptor antagonist yohimbine (Sigma; 5 mg/kg; n=6), or the benzodiazepine receptor inverse partial agonist FG-7142 (Tocris, Avonmouth, UK; 7.5 mg/kg; n=6). All drugs were dissolved in 0.9% saline, except for FG-7142, which was dissolved in 0.9% saline/40% 2-hydroxypropyl-cyclodextrin (Tocris) to increase solubility as in previous studies (Singewald et al., 2003; Singewald and Sharp, 2000). Each individual cage was placed under a video camera (model WVBP100B\W, Panasonic, Bracknell, UK). Behavior was recorded using an eight-way Sprite multiplex video playback system and 24-h time lapse VCR (Philips-LDH8256-D and HS5424; Philips Communication, Security & Imaging B.V., Eindhoven, The Netherlands). Behavior was taped from 30 min before injection until 2 h after injection. Rats were then anesthetized i.p. with sodium pentabarbitone (0.65 mg/kg) and transcardially perfused with 4% paraformaldehyde in 0.1 M sodium phosphate buffer (PB). All buffers used were pH 7.4. Brains were removed, post-fixed in the same fixative for 12 h, rinsed twice in PB (12 h), and placed in buffer comprising 30% sucrose in 0.1 M PB for 12 h. Brain tissues were blocked using a standard adult rat brain matrix (model RBM-4000C, ASI Instruments) and frozen using liquid isopentane cooled by liquid nitrogen.

Statistical Analyses of Single ORX-ir and Double c-Fos/ORX-ir Neurons in and ORX mRNA The dependent variables for cell counts (number of single ORXA-ir and double c-Fos/ORXA-ir cells) were analysed using a one-way ANOVA with gas exposure as the between-subjects factor and hypothalamic region as the repeated measure. In the presence of significant main effects or main effect×brain region interactions, post-hoc tests were conducted to define the anatomical location of the effects using an unpaired two-tailed t-test. In Experiment 12, ppORX mRNA expression from each treatment group was compared using an unpaired t-test. Statistical significance was accepted at $p<0.05$.

Example

Experiment 13: Effects of an ORX1 Receptor Antagonist on FG-7142-Induced Anxiety and Brain Responses Animals and Housing Conditions All experiments were conducted on adult male Wistar rats (250-300 g) purchased from Harlan Laboratories (Indianapolis, Ind. USA) and were housed individually in plastic cages under standard environmental conditions (22° C.; 12/12 light/dark cycle; lights on at 7:00 A.M.) for 7-10 days prior to the surgical manipulations. Food and water were provided ad libitum.

In this experiment, rats were split into 3 drug treatment groups (n=8/group), where the rats each received the following: group 1) a vehicle injection (0.2 ml DMSO in 100 g volume dH$_2$O) followed by another vehicle (0.2 ml DMSO/0.1 ml TWEEN80 in 100 g volume dH$_2$O) with injection; group 2) a vehicle injection followed by an inverse benzodiazepine agonist (FG-7142, 7.5 mg/kg ip, Sigma); or in group 3) an orexin 1 receptor antagonist (SB334867, 30 mg/kg ip, Tocris) followed by FG-7142. Fifteen min after the FG-7142 injection, all rats were tested for anxiety behavior using a 5 min open field test (OFT); 5 min social interaction (SI) test; then a 5 min elevated plus maze (EPM) test. Ninety min following FG-7142 injections, rats were anaesthetized and then the brains were removed and processed for immunohistochemistry as described in detail in subsequent section.

Open-Field Behavior Anxiety Test (OFT)

The open-field arena covered an area of 90 cm×90 cm, with 40 cm high walls. The open-field arena was divided into a 6×6 grid of equally-sized squares using black tape (36 total squares) with 4 squares forming the centre; 12 squares forming the middle perimeter; and 20 squares forming the outer perimeter. The test started by placing a rat in the centre. The behavior of each rat in the open-field arena was recorded on video and scored afterwards by an observer blind to the experimental treatment of each rat. Time spent in each region of the open-field was recorded. In addition, locomotor activity was assessed by counting the number of times the rat's entire body (excluding tail) completely crossed into another square.

Social Interaction Anxiety Test (SI)

A modified version of the social interaction (SI) test (File, 1980) was utilized to measure anxiety-like responses. Following the OFT, the experimental rat was placed in an open field (0.9 m long×0.9 m wide with walls 0.3 m high) with an untreated novel partner rat. A video camera was fixed above the box, and all behavioral tests were videotaped. During the 5 min test the total amount of time the treated rat initiates interaction with the partner rat is recorded (sniffing, grooming etc.) as described previously. Videotaped sessions were scored at a later time by a SDF (blind to treatments) and a decrease in total interaction time was taken as an increase in "anxiety" like behavior.

Elevated Plus Maze Anxiety Test (EPM)

Following the SI test, rats were place in the center area of the EPM where the two arms intersect. Unlike the SI test, the EPM measures many relevant anxiety related behaviors such as: no. of poke and full entries into and duration spent in closed versus open arm. The arena dimensions are the following: each arm is 4.25" wide and 19.75" long, intersection is 4.25" by 4.25", closed walls are 15.75" high. Activity is measured using 38 state of the art photobeams (16× beams and 16 Y beams) to provide the highest resolution system available (Automated EPM, Hamilton Kinder Scientific, San diego, CA).

Perfusion

Ninety min following the initiation of treatment, rats were anaesthetised with an overdose of sodium pentobarbital (40 mg, i.p.) then perfused transcardially with 0.05 M phosphate buffered saline (PBS; 250 ml), followed by 0.1 M sodium phosphate buffer (PB; 250 ml) containing 4% paraformaldehyde (PFA) and 3% sucrose. Brains were removed and post-fixed for 24 h in the same fixative, rinsed for 24 h in 0.1 M PB, then placed in cryoprotectant (30% sucrose in 0.1 M PB) for an additional 4-5 days. To maintain a consistent plane for coronal sections, brains were placed in a rat brain matrix (ASI instruments, Model No. RBM-4000C) and cut with a razor blade at the caudal border of the mammillary bodies. Brains were frozen in cooled liquid isopentane made by immersing a plastic vessel containing isopentane into a dewar flask containing liquid nitrogen. Serial coronal sections (30 µm) were cut using a cryostat and were immediately placed in cryoprotectant consisting of 27% ethylene glycol and 16% glycerol in 0.05 M PB to yield six alternate sets of sections. Sections were stored at −20° C. until immunohistochemical processing. All solutions had a pH of 7.4.

All brain sections were immunostained with the c-Fos primary antibody in a single immunohistochemical run, rather than in batches, with large volume incubations to limit variability in the quality of immunohistochemical staining among brain sections. However, the forebrain was immunostained for c-Fos in one run and the brainstem (i.e., midbrain, pons and medulla) in another. Immunostaining for c-Fos protein was accomplished using an affinity-purified primary antibody directed at c-Fos (rabbit anti-human c-Fos polyclonal affinity-purified antibody, Cat. no. sc-52, Santa Cruz Biotechnology, San Diego, Calif.; diluted 1:10,000). Free-floating sections were washed in 0.1 M PBS for 30 min, then incubated in 1% $H_2O_2$ in PBS for 20 min. Sections were then washed 10 min in PBS and 20 min in PBS with 0.3% Triton X-100 (PBST). Sections were then incubated 12-16 h in PBST with primary antibody solution at room temperature. After a 30 min wash in PBST, sections were incubated for 2 hr in biotinylated goat anti-rabbit IgG (Cat no. BA-1000, Vector Laboratories, Burlinghame, Calif.; diluted 1:500). Sections were washed again for 30 min in PBST then incubated 1.5 hr in an avidin-biotin-peroxidase complex provided in a standard Vector Elite kit (Cat no. PK-6100, Vector Laboratories, diluted 1:200). The peroxidase substrate for the chromogen reaction was Vector SG, which was prepared as recommended by the manufacturer (Cat. no. SK-4700, Vector Laboratories). The substrate reaction was run for 20 min for the forebrain. All sections were mounted on clean glass slides, dried overnight, dehydrated and mounted with coverslips using DPX mounting medium (BDH Laboratory Supplies, Poole, UK). All washes and incubations were done at room temperature in 12-well polystyrene plates with low frequency shaking on an orbital shaker.

Cell Counts

Selection of anatomical levels for analysis of c-Fos-immunostained cells was conducted with reference to illustrations from a rat brain stereotaxic atlas (Paxinos and Watson, 1997). Selection of anatomical levels was also done in reference to major anatomical landmarks including white matter tracts and the ventricular systems. Specifically, darkfield contrast [i.e., using a 1.6× Leica phase contrast Plan objective and Leica binocular microscope (model DMLB, Leica Mikroskopie and Systeme GmbH, Wetzler, Germany) with a darkfield condenser] was used to visualise white matter tracts (e.g., the formix and optic tracts) and ventricular systems (e.g., lateral, $3^{rd}$ and $4^{th}$ ventricles) that aided in selection of appropriate coronal levels with reference to illustrations in a standard stereotaxic atlas of the rat brain (Paxinos and Watson, 1997). The numbers of c-Fos-ir cells were counted in the entire field of view at 400× magnification (i.e., 10× eyepiece and 40× Plan objective) for each brain region. The regions selected for analysis were as follows: bed nucleus of the stria terminalus (BNST) divisions (at +0.20 and −0.30 mm from bregma), and the intermediate part of lateral septum (LSI: at +0.20 and −0.30 mm from bregma), the paraventicular hypothalamic nucleus (PVN: −1.80 mm from bregma); the amygdala subdivisions [central amygdaloid nucleus (CeA); basolateral amygdaloid nucleus, anterior part (BLA); lateral amygdaloid nucleus (LA); and the medial amygdaloid nucleus (MeA) at −2.56 mm from bregma]; and the dorsomedial hypothalamus (DMH), the periformical nucleus (PeF) (−3.14 mm from bregma), All cell counts were done by an observer (PLJ) that was blind to the experimental treatment of each animal.

Statistical Analyses

Analyses of Open-Field Behavior

Dependent variables for the open-field test (i.e., time spent in each section) were analysed using paired 2-tailed t-tests were used for post-hoc pairwise comparisons since each rat received both atmospheric and hypercarbic gas infusions on different days. The two-tailed alpha level was set at $P<0.05$ in all cases.

Statistical Analyses of Cell Counts

The dependent variable for cell counts (number of c-Fos-ir cells) was analyzed using a multifactor ANOVA with repeated measures with gas exposure as the between-subjects factor and brain region as the within-subjects factor. Missing values for multifactor ANOVAs with repeated measures were calculated using the Peterson method (Peterson, 1985); these values were not included in further post-hoc tests or in graphical representations of the data. Missing values for c-Fos-ir cell counts included 13 missing values out of 462 total values (approximately 2.8%). In the presence of significant main effects or main effect×brain region interactions, post-hoc tests were conducted to define the anatomical location of the effects using Fisher's Protected Least Significant Difference (Fisher's PLSD) tests for comparison of different subjects. Statistical significance was accepted at $P<0.05$. All statistical analyses were carried out using SYSTAT 5.02 (SYSTAT Inc., San Jose, Calif.) and SPSS14.0 (SPSS Inc., Chicago, Ill.), and all graphs were generated using SigmaPlot 2001 (SPSS Inc.) and an illustration program (CorelDraw 11.633 for Windows, Viglen Ltd., Alperton, Middlesex, UK).

Photography

Photomicrographs were obtained using a brightfield microscope using N Plan 5×, 10×, 40× and 63× objective lenses (Leica binocular microscope, model DMLB), an Insight digital camera (Diagnostics Instruments Inc., Sterling Heights, Mich., USA) and SPOT 3:5.5 for Windows digital imaging software (Silicon Graphics, Mountain View, Calif., USA). Photographic plates were prepared in CorelDraw 11.633 for Windows.

Results

Figure 35:
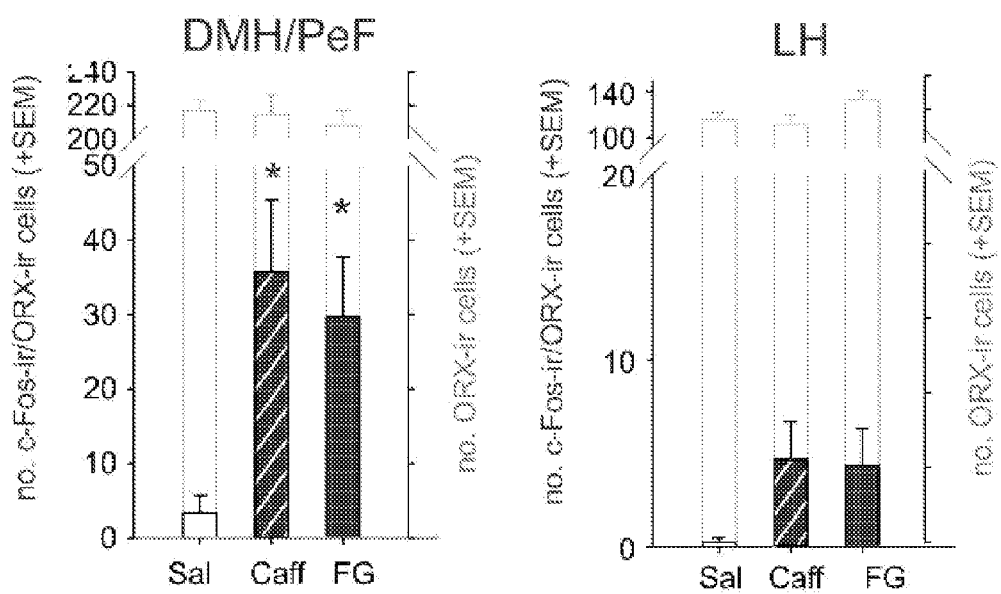
FIG. 35 shows number of c-Fos immunoreactive and orexin immunoreactive cells in DMH/PeF and LH hypothalamic regions following treatment with saline (Sal), caffeine (Gaff) or FG-7142 (FG).
Figure 36:
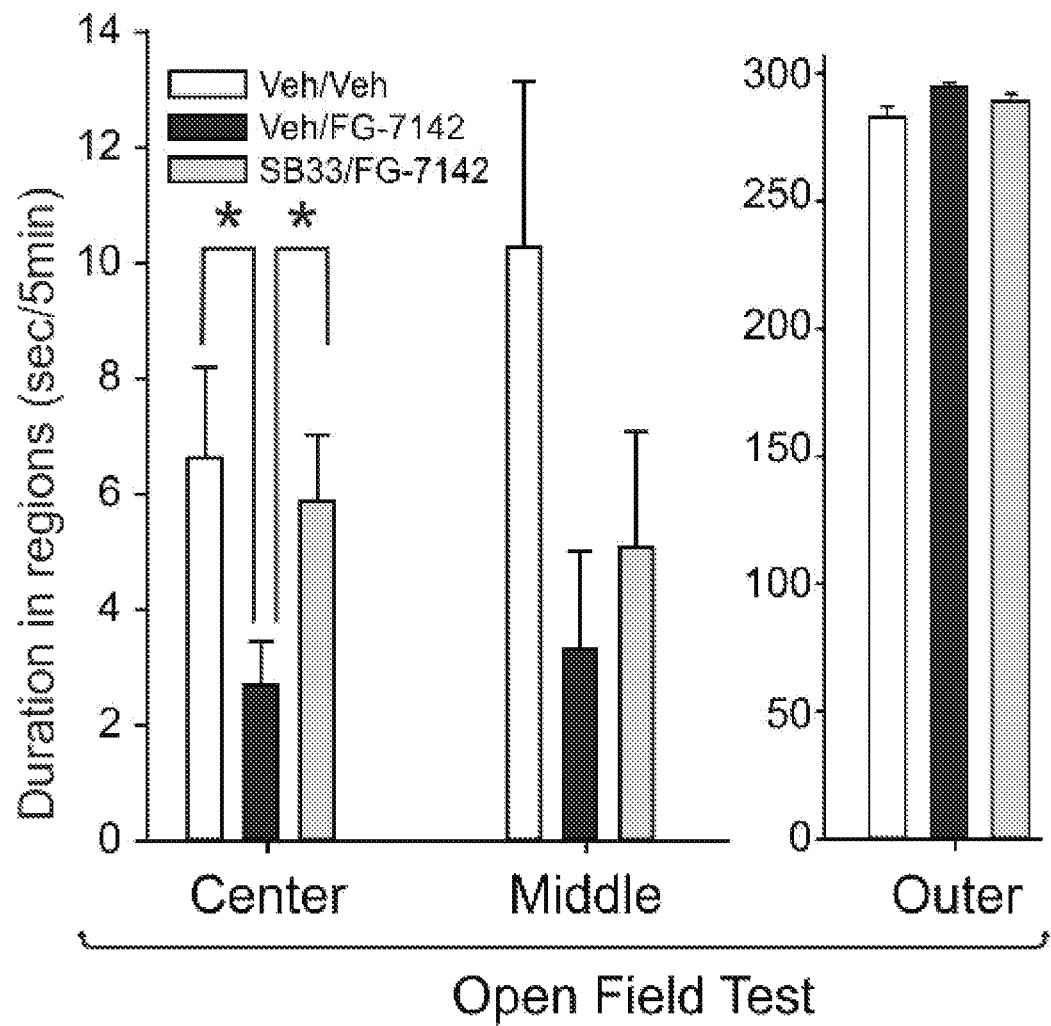
FIG. 36 shows open field test results in response to challenge with vehicle (Veh) or FG-7142 in rats pre-treated with vehicle or SB334867 (SB33).
Figure 37:
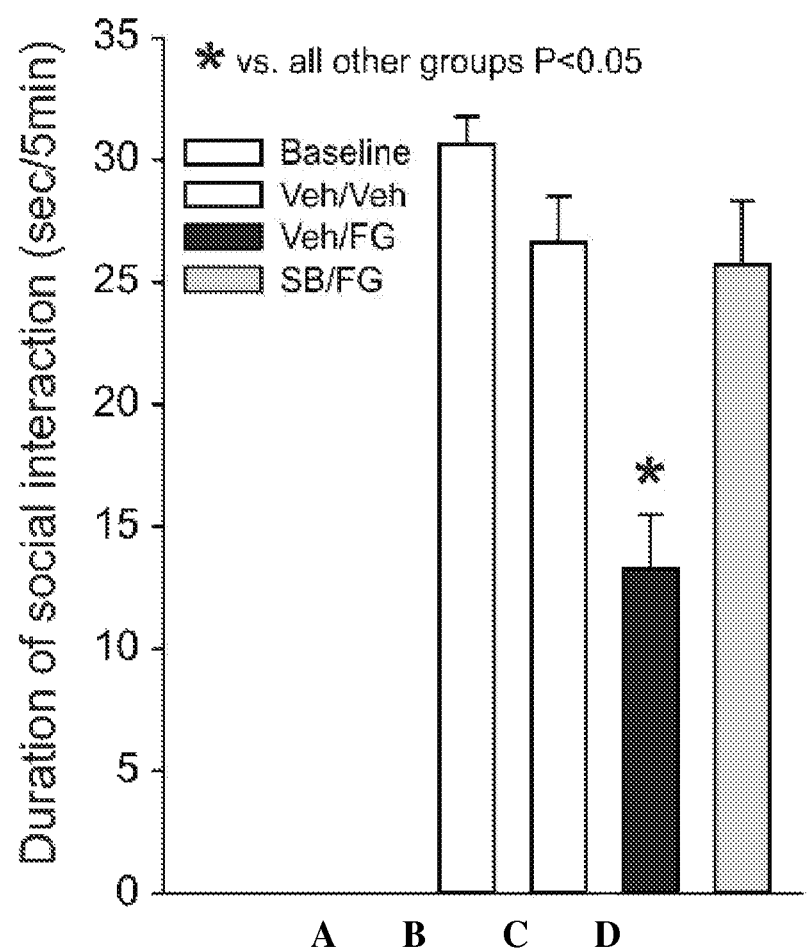
FIG. 37 shows social interaction at baseline and in response to challenge with vehicle (Veh) or FG-7142 in rats pre-treated with vehicle or SB334867 (SB33). A=baseline; B=Veh/Veh; C=Veh/FG; D=SB/FG.
Figure 38:
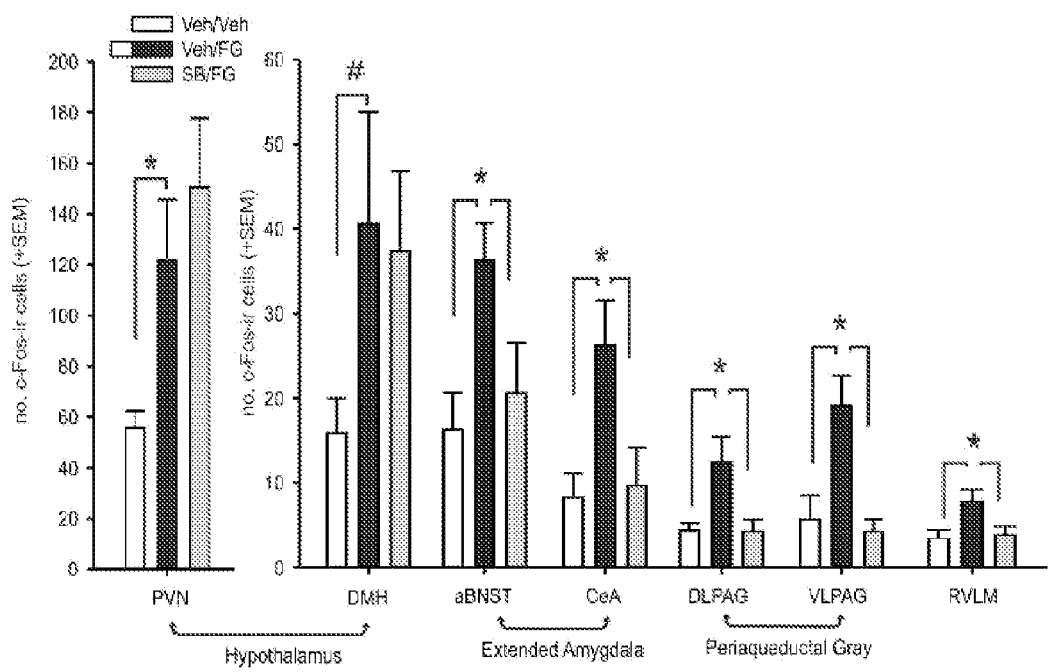
FIG. 38 shows number of c-Fos immunoreactive cells in hypothalamic, extended amygdala, periaqueductal grey, and rostral ventrolateral medulla brain regions in response to challenge with vehicle (Veh) or FG-7142 (FG) in rats pre-treated with vehicle or SB334867 (SB33).

Using immunohistochemistry, both anxiogenic compounds increased cellular responses in hypothalamic orexin neurons (FIG. 35). In the open field test, the orexin 1 antagonist appeared to have attenuated FG-7142 induced anxiety (FIG. 36). In the social interaction test, the orexin 1 receptor antagonist blocked FG-7142-induced anxiety behavior (FIG. 37). In the elevated plus maze, anxiety behavior was noted in vehicle treated control and in the FG-7142 group (evidenced by low open arm times). This may be due to the repeated anxiety testing. However, the orexin 1 antagonist treated rats had higher time in open arms indicative of an anxiolytic action.

TABLE 2

Mean number of c-Fos immunoreactive cells
in brain regions in response to treatments.

| single c-Fos-ir cells | veh/veh | veh/FG | SB/FG |
|---|---|---|---|
| ILC (+2.60 mm bregma) | 12 ± 2 | 12 ± 6 | 14 ± 8 |
| PRL (+2.60 mm bregma) | 5 ± 2 | 3 ± 1 | 2 ± 0 |
| LSI (+0.20 mm bregma) | 16 ± 4 | 12 ± 4 | 10 ± 4 |
| PeF (−3.14 mm bregma) | 31 ± 8 | 67 ± 23 | 65 ± 20 |
| Amygdala (−2.56 mm bregma) | | | |
| BLA | 8 ± 4 | 9 ± 4 | 6 ± 2 |
| MeA | 72 ± 14 | 85 ± 18 | 91 ± 21 |
| LA | 7 ± 2 | 10 ± 4 | 6 ± 1 |
| DRN (−7.80 mm bregma) | 1 ± 0 | 1 ± 0 | 1 ± 0 |
| lPBN (−9.30 mm bregma) | 11 ± 7 | 9 ± 3 | 10 ± 3 |
| mPBN (−9.30 mm bregma) | 3 ± 1 | 3 ± 1 | 2 ± 1 |
| LC (−10.04 mm bregma) | 45 ± 8 | 48 ± 5 | 45 ± 9 |

The invention claimed is:

1. A method of treating hypercapnia-induced anxiety associated with chronic obstructive pulmonary disease in an individual, the method comprising administering to the individual suffering from chronic obstructive pulmonary disease a composition comprising a therapeutically effective amount of an agent to down regulate the activity of an orexin, Orexin A, wherein the agent is an orexin receptor antagonist for orexin 1 receptors; wherein the effective amount treats hypercapnia-induced anxiety associated with chronic obstructive pulmonary disease in the individual wherein the effective amount treats hypercapnia-induced anxiety without altering the robust bradycardia response.

2. The method of claim 1, wherein the orexin receptor antagonist is selected from SB334867, and SB408124.

3. The method of claim 1, wherein the orexin receptor antagonist comprises about 30 mg/kg.

4. The method of claim 1, wherein the orexin receptor antagonist is administered by a route selected from the group consisting of orally and parenterally.

5. The method of claim 1, wherein the orexin receptor antagonist is administered by a route selected from the group consisting of intranasally, inhalable, intramuscularly, intraperitoneally; intravenously, intraventricularly, intraspinally, intrarectally, ipsalaterally and subcutaneously.

* * * * *